(12) United States Patent
Casscells et al.

(10) Patent No.: US 6,214,001 B1
(45) Date of Patent: Apr. 10, 2001

(54) ELECTROCAUTERIZING TOOL FOR ORTHOPEDIC SHAVE DEVICES

(75) Inventors: Christopher D. Casscells, Greenville, DE (US); Ramiro L. Reyes, Union City; Hugh R. Sharkey, Woodside, both of CA (US)

(73) Assignee: Oratec Interventions, Inc., Menlo Park, CA (US)

( * ) Notice: Subject to any disclaimer, the term of this patent is extended or adjusted under 35 U.S.C. 154(b) by 0 days.

(21) Appl. No.: 09/066,615

(22) Filed: Apr. 24, 1998

Related U.S. Application Data

(60) Provisional application No. 60/059,383, filed on Sep. 19, 1997.

(51) Int. Cl.$^7$ .................................................... A61B 18/18
(52) U.S. Cl. .............................. 606/41; 606/45; 606/49; 606/180
(58) Field of Search ................................ 606/41, 45, 46, 606/49, 50, 180; 604/22

(56) References Cited

U.S. PATENT DOCUMENTS

| 2,090,923 | 8/1937 | Wappler | 128/303.15 |
|---|---|---|---|
| 3,178,728 | 4/1965 | Christensen | 3/1 |
| 3,579,643 | 5/1971 | Morgan | 3/1 |
| 3,776,230 | 12/1973 | Neefe | 128/260 |
| 3,856,015 | 12/1974 | Iglesias | 128/303.15 |
| 3,867,728 | 2/1975 | Substad et al. | 3/1 |
| 3,879,767 | 4/1975 | Substad | 3/1 |
| 3,886,600 | 6/1975 | Kahn et al. | 3/1 |
| 3,938,198 | 2/1976 | Kahn et al. | 3/1.912 |
| 3,945,375 | 3/1976 | Banko | 128/6 |
| 3,987,499 | 10/1976 | Scharbach et al. | 3/1.91 |
| 3,992,725 | 11/1976 | Homsy | 3/1 |
| 4,043,342 | 8/1977 | Morrison, Jr. | 128/303.14 |
| 4,074,718 | 2/1978 | Morrison, Jr. | 128/303.14 |
| 4,085,466 | 4/1978 | Goodfellow et al. | 3/1.91 |
| 4,129,470 | 12/1978 | Homsy | 156/155 |
| 4,134,406 | 1/1979 | Iglesias | 128/303.15 |
| 4,224,696 | 9/1980 | Murray et al. | 3/1.911 |
| 4,224,697 | 9/1980 | Murray et al. | 3/1.911 |
| 4,326,529 | 4/1982 | Doss et al. | 128/303.1 |
| 4,344,193 | 8/1982 | Kenny | 3/1.911 |
| 4,362,160 | 12/1982 | Hiltebrandt | 128/303.15 |
| 4,375,220 | 3/1983 | Matvias | 128/804 |
| 4,381,007 | 4/1983 | Doss | 128/303.1 |

(List continued on next page.)

FOREIGN PATENT DOCUMENTS

| 3511107A1 | 10/1986 | (DE) | A61B/17/39 |
|---|---|---|---|
| 3632197A1 | 3/1988 | (DE) | A61B/10/00 |
| 39 18316 | 3/1990 | (DE) | A61B/17/39 |

(List continued on next page.)

OTHER PUBLICATIONS

Beadling, L., "Bi–Polar electrosurgical devices: Sculpting the future of arthroscopy", *Orthopedics today*, vol. 17, No. 1, Jan. 1997, 4 pages.

(List continued on next page.)

*Primary Examiner*—Lee Cohen
*Assistant Examiner*—R. Kearney
(74) *Attorney, Agent, or Firm*—David J. Weitz, Wilson Sonsini. Goodrich & Rosati

(57) ABSTRACT

Disclosed is a surgical apparatus including a surgical instrument including a housing and a cannula, and a surgical tool including a shaft and a tip, and a drive interface and an electrical interface, and the drive interface producing a surgical motion of the tip, and the electrical interface producing a cauterizing action of the tip. Also disclosed is a cutting and cauterizing device for connection to a surgical instrument. Additionally, methods for using both the surgical apparatus and the cutting and cauterizing device are disclosed.

33 Claims, 16 Drawing Sheets

U.S. PATENT DOCUMENTS

| | | | |
|---|---|---|---|
| 4,397,314 | 8/1983 | Vaguine | 128/399 |
| 4,476,862 | 10/1984 | Pao | 128/303.17 |
| 4,483,338 | 11/1984 | Bloom et al. | 128/303.13 |
| 4,517,965 | 5/1985 | Ellison | 128/20 |
| 4,517,975 | 5/1985 | Garito et al. | 128/303.13 |
| 4,532,924 * | 8/1985 | Auth et al. | 606/50 |
| 4,590,934 | 5/1986 | Malis et al. | 128/303.14 |
| 4,593,691 | 6/1986 | Lindstrom et al. | 128/303.14 |
| 4,597,379 | 7/1986 | Kihn et al. | 128/1 R |
| 4,601,705 | 7/1986 | McCoy | 604/94 |
| 4,651,734 | 3/1987 | Doss et al. | 128/303.14 |
| 4,811,733 | 3/1989 | Borsanyi et al. | 128/303.14 |
| 4,815,462 | 3/1989 | Clark | 128/305 |
| 4,838,859 | 6/1989 | Strassmann | 604/95 |
| 4,846,175 | 7/1989 | Frimberger | 128/303.15 |
| 4,873,976 | 10/1989 | Schreiber | 128/334 R |
| 4,894,063 | 1/1990 | Nashef | 623/13 |
| 4,895,148 | 1/1990 | Bays et al. | 606/213 |
| 4,907,585 | 3/1990 | Schachar | 606/28 |
| 4,907,589 | 3/1990 | Cosman | 606/34 |
| 4,924,865 | 5/1990 | Bays et al. | 606/77 |
| 4,944,727 | 7/1990 | McCoy | 604/95 |
| 4,950,234 | 8/1990 | Fujioka et al. | 604/60 |
| 4,955,882 | 9/1990 | Hakky | 606/14 |
| 4,966,597 | 10/1990 | Cosman | 606/50 |
| 4,976,709 | 12/1990 | Sand | 606/5 |
| 4,976,715 | 12/1990 | Bays et al. | 606/77 |
| 4,998,933 | 3/1991 | Eggers et al. | 606/41 |
| 5,007,908 | 4/1991 | Rydell | 606/47 |
| 5,009,656 | 4/1991 | Reimels | 606/48 |
| 5,085,657 | 2/1992 | Ben-Simhon | 606/42 |
| 5,085,659 | 2/1992 | Rydell | 606/47 |
| 5,098,430 | 3/1992 | Fleenor | 606/42 |
| 5,100,402 | 3/1992 | Fan | 606/41 |
| 5,103,804 | 4/1992 | Abele et al. | 128/4 |
| 5,114,402 | 5/1992 | McCoy | 604/95 |
| 5,152,748 | 10/1992 | Chastagner | 604/95 |
| 5,178,620 | 1/1993 | Eggers et al. | 606/41 |
| 5,186,181 | 2/1993 | Franconi et al. | 128/804 |
| 5,191,883 | 3/1993 | Lennox et al. | 128/401 |
| 5,192,267 | 3/1993 | Shapira et al. | 604/22 |
| 5,201,729 | 4/1993 | Hertzmann et al. | 606/2 |
| 5,201,730 | 4/1993 | Easley et al. | 606/4 |
| 5,201,731 | 4/1993 | Hakky | 606/15 |
| 5,213,097 | 5/1993 | Zeindler | 128/401 |
| 5,230,334 | 7/1993 | Klopotek | 128/399 |
| 5,242,439 | 9/1993 | Larsen et al. | 606/15 |
| 5,242,441 | 9/1993 | Avitall | 606/41 |
| 5,261,906 | 11/1993 | Pennino et al. | 606/46 |
| 5,267,994 | 12/1993 | Gentelia et al. | 606/15 |
| 5,275,151 | 1/1994 | Shockey et al. | 128/4 |
| 5,279,559 | 1/1994 | Barr | 604/95 |
| 5,284,479 | 2/1994 | de Jong | 604/60 |
| 5,304,169 | 4/1994 | Sand | 606/5 |
| 5,308,311 | 5/1994 | Eggers et al. | 606/28 |
| 5,311,858 | 5/1994 | Adair | 128/4 |
| 5,320,115 | 6/1994 | Kenna | 128/898 |
| 5,323,778 | 6/1994 | Kandarpa et al. | 128/653.2 |
| 5,334,193 | 8/1994 | Nardella | 606/41 |
| 5,342,357 | 8/1994 | Nardella | 606/40 |
| 5,348,554 | 9/1994 | Imran et al. | 606/41 |
| 5,352,868 | 10/1994 | Denen et al. | 219/501 |
| 5,354,331 | 10/1994 | Schachar | 623/4 |
| 5,364,395 | 11/1994 | West, Jr. | 606/46 |
| 5,366,443 | 11/1994 | Eggers et al. | 604/114 |
| 5,366,490 | 11/1994 | Edwards et al. | 607/99 |
| 5,382,247 | 1/1995 | Cimino et al. | 606/33 |
| 5,397,304 | 3/1995 | Truckai | 604/95 |
| 5,401,272 | 3/1995 | Perkins | 606/15 |
| 5,415,633 | 5/1995 | Lazarus et al. | 604/95 |
| 5,423,806 | 6/1995 | Dale et al. | 606/15 |
| 5,433,739 | 7/1995 | Sluijter et al. | 607/99 |
| 5,437,661 | 8/1995 | Rieser | 606/15 |
| 5,437,662 | 8/1995 | Nardella | 606/40 |
| 5,451,223 | 9/1995 | Ben-Simhon | 606/42 |
| 5,458,596 | 10/1995 | Lax et al. | 606/31 |
| 5,464,023 | 11/1995 | Viera | 128/772 |
| 5,465,737 | 11/1995 | Schachar | 128/898 |
| 5,484,403 | 1/1996 | Yoakum et al. | 604/59 |
| 5,484,432 | 1/1996 | Sand | 606/5 |
| 5,484,435 | 1/1996 | Fleenor et al. | 606/46 |
| 5,487,757 | 1/1996 | Truckai et al. | 607/122 |
| 5,498,258 | 3/1996 | Hakky et al. | 606/15 |
| 5,500,012 | 3/1996 | Brucker et al. | 607/122 |
| 5,507,812 | 4/1996 | Moore | 623/13 |
| 5,514,130 | 5/1996 | Baker | 606/41 |
| 5,524,338 | 6/1996 | Martyniuk et al. | 29/825 |
| 5,527,331 | 6/1996 | Kresch et al. | 606/170 |
| 5,542,920 | 8/1996 | Cheikh | 604/57 |
| 5,569,242 | 10/1996 | Lax et al. | 606/42 |
| 5,599,346 | 2/1997 | Edwards et al. | 606/41 |
| 5,630,839 | 5/1997 | Corbett, III et al. | 607/137 |
| 5,681,282 | 10/1997 | Eggers et al. | 604/114 |
| 5,683,366 | 11/1997 | Eggers et al. | 604/114 |
| 5,688,270 | 11/1997 | Yates et al. | 606/51 |
| 5,697,909 | 12/1997 | Eggers et al. | 604/114 |
| 5,718,702 | 2/1998 | Edwards | 606/41 |
| 5,782,795 | 7/1998 | Bays | 606/22 |
| 5,810,809 | 8/1998 | Rydell | 606/49 |
| 6,007,533 * | 12/1999 | Casscells et al. | 606/45 |

FOREIGN PATENT DOCUMENTS

| | | | |
|---|---|---|---|
| 0 257 116 A1 | 3/1988 | (EP) | A61N/1/36 |
| 0 274 705 A1 | 7/1988 | (EP) | A61M/23/00 |
| 0 479 482 A1 | 4/1992 | (EP) | A61B/17/39 |
| 0 521 595 A2 | 1/1993 | (EP) | A61M/25/01 |
| 0 542 412 A1 | 5/1993 | (EP) | A61B/17/39 |
| 0 558 297 A2 | 9/1993 | (EP) | A61M/25/00 |
| 0 566 450 A1 | 10/1993 | (EP) | A61N/5/02 |
| 0 572 131 A1 | 12/1993 | (EP) | A61B/17/39 |
| 0 682 910 A1 | 11/1995 | (EP) | A61B/1/00 |
| 0 479 482 B1 | 5/1996 | (EP) | A61B/17/39 |
| 0 729 730 A1 | 9/1996 | (EP) | A61B/17/32 |
| 0 737 487 A2 | 10/1996 | (EP) | A61M/25/01 |
| 0 783 903 A1 | 7/1997 | (EP) | A61N/5/04 |
| 1122634 | 9/1956 | (FR) | A61F/19/00 |
| 2 645 008 | 3/1989 | (FR) | A61B/17/32 |
| 2 645 008 | 10/1990 | (FR) | A61B/17/32 |
| 1 340 451 | 12/1973 | (GB) | A61F/1/00 |
| 2 164 473 | 3/1986 | (GB) | A61B/17/36 |
| 5-42166 | 5/1993 | (JP) | A61B/17/39 |
| 637118 | 12/1978 | (SU) | A61B/17/18 |
| WO 82/02488 | 8/1982 | (WO) | A61B/17/39 |
| WO 85/02762 | 7/1985 | (WO) | A61B/17/36 |
| WO 92/05828 | 4/1992 | (WO) | A61M/25/00 |
| WO 92/10142 | 6/1992 | (WO) | A61B/17/36 |
| WO 93/01774 | 2/1993 | (WO) | A61F/7/12 |
| WO 93/16648 | 9/1993 | (WO) | A61B/17/32 |
| WO 93/20984 | 10/1993 | (WO) | B26D/1/11 |
| WO 95/01814 | 1/1995 | (WO) | A61N/5/02 |
| WO 95/10981 | 4/1995 | (WO) | A61B/8/12 |
| WO 95/13113 | 5/1995 | (WO) | A61N/5/02 |
| WO 95/18575 | 7/1995 | (WO) | A61B/17/39 |
| WO 95/20360 | 8/1995 | (WO) | A61B/17/39 |
| WO 95/25471 | 9/1995 | (WO) | A61B/17/39 |
| WO 95/30373 | 11/1995 | (WO) | A61B/17/00 |
| WO 95/30377 | 11/1995 | (WO) | A61B/17/39 |
| WO 95/34259 | 12/1995 | (WO) | A61F/5/48 |
| WO 96/11638 | 4/1996 | (WO) | A61B/17/32 |
| WO 96/32051 | 10/1996 | (WO) | A61B/1/00 |
| WO 96/32885 | 10/1996 | (WO) | A61B/5/04 |

| | | | |
|---|---|---|---|
| WO 96/34559 | 11/1996 | (WO) | A61B/5/0402 |
| WO 96/34568 | 11/1996 | (WO) | A61B/17/36 |
| WO 96/34571 | 11/1996 | (WO) | A61B/17/39 |
| WO 96/39914 | 12/1996 | (WO) | A61B/1/00 |
| WO 97/06855 | 2/1997 | (WO) | A61N/1/40 |
| WO 98/07468 | 2/1998 | (WO) | A61N/1/40 |
| WO 98/17190 | 4/1998 | (WO) | A61B/18/00 |

OTHER PUBLICATIONS

Ellman International Mfg., Inc., 1989, Catalog, pp. 1–15, 20.

Cosset, J.M., Resistive Radiofrequency (Low Frequency) Interstitial Heating (RF Technique), Interstitial Hyperthermia, Dec. 6, 1993, pp. 3–5, 37.

Attachment I: Competitive Literature on Generators with Bipolar Capabilities, IME Co., Ltd., pp. 60–86.

Attachment II: Competitive Literature on Bipolar Forceps and Footswitch Controls, IME Co., Ltd. pp. 87–104.

Christian, C. et al., "Allograft Anterior Cruciate Ligament Reconstruction with Patellar Tendon: An Endoscopic Technique", *Operative Techniques in Sports Medicine*, vol. 1, No. 1, Jan. 1993, pp. 50–57.

Houpt, J. et al., "Experimental Study of Temperature Distributions and Thermal Transport During Radiofrequency Current Therapy of the Intervertebral Disc", *Spine*, vol. 21, No. 15, (1996), pp. 1808–1813.

Troussier, B. et al., "Percutaneous Intradiscal Radio–Frequency Thermocoagulation: A Cadaveric Study", *Spine*, vol. 20, No. 15, (Aug. 1995), pp. 1713–1718.

Auhll, Richard A., "The Use of the Resectoscope in Gynecology." Biomedical Business International, Oct. 11, 1990, pp. 91–93.

Trimedyne, The Less Invasive Laser Advantage, Omni Spinal Introduction System.

PRNewswire ( Dec. 12, 1994), Two Physicians Perform First Outpatient Cervical Disc Procedure Using Laser Technology.

Introduction to the LDD Disc Kit, Oct. 16, 1996.

Mayer et al., Lasers in Percutaneous Disc Surgery: Beneficial Technology or Gimmick?, vol. 25 No.251 (1993) pp. 38–44.

Schatz et al., Preliminary Experience With Percutaneous Laser Disc Decompression in the Treatment of Sciatica, vol. 38 No. 5, Oct. 1995, pp. 432–436.

Savitz M. A., Same–day Microsurgical Arthroscopic lateral–approach Laser–assisted (Small) Fluoroscopic Discectomy, vol. 80, Jun. 1994 pp. 1039–1045.

Basacco et al., Functional Results of Percutaneous Laser Discectomy, Dec. 1996, pp. 825–828.

Sluijter M.E., The Use of Radiofrequency lesions For Pain Relief in Failed Back Patients, vol. 10 No. 1 (1988).

Cosman et al., Theoretical Aspects of Radiofrequency lesions in the Dorsal Root Entry Zone, vol. 15 No. 6 (1984) pp. 945–950.

Wilkins et al., Neurosurgery: Method of Making Nervous System Lesions, ch. 337, pp. 2490–2499.

Yonezawa et al., The System and Procedure of percutaneous Intradiscal Laser Nucleotomy, vol. 15 No. 5 (1990) pp. 1175–1185.

Kolarik et al., Photonucleolysis of Intervertebral Disc and it's Herniation, (1990).

Gottlob et al.,Lasers In Surgery and Medicine: Holmium: YAG Laser Ablation of Human Intervertebral Disc: Preliminary Evaluation, vol. 12, (1991) pp. 86–91.

Buchelt et al., Lasers in Surgery and Medicine: Fluorescence Guided Excimer Laser Ablation of Intervertebral Discs In Vitro, vol. 11, (1991) pp. 280–286.

Choy et al., Percutaneous Laser Disc Decompression: A New Therapeutic Modality, vol. 17 No. 8, (1992) pp. 949–956.

Sluijter et al., Persistant Pain, Modern Methods of Treatment: Treatment of Chronic Back and neck Pain, vol. 3, (1981) pp. 141–179.

Sluijter, Int Disabil Studies: The use of Radio Frequency Lesions For Pain Relief in Failed Back, vol. 10, Sep. 4, 1996, pp. 37–43.

Shatz et al., CJS JCC Preliminary Experience With Percutaneous Laser Disc Decompression in the Treatment of Sciatica, vol. 38 No. 5, Oct. 1995 pp. 432–436.

Gerber et al., Der Orthopade: Offene Laserchirurgie am Bewegungsapparat, vol. 25, (1996) pp. 56–63.

Sluyter, Radiofrequency Lesions in the Treatment of Cervical Pain Syndromes, Radionics, Inc. (1989).

Kelly L.E., Purification and Properties of a 23kDa Ca2+ –binding Protein, (1990) 271, pp. 661–666.

Gehring W. J., Exploring the Homeobox, (1993), pp. 215–221.

Buchelt et al., Lasers in Surgery and Medicine:Erb:YAG and Hol:YAG Laser Ablation of Meniscus and Intervertebral Discs, vol. 12 No. 4, (1992) pp. 375–381.

Leu et al., Der Orthopade: Endoskopie der Wirbelsaule: Minimal–invasive Therapie, vol. 21,(1992) pp. 267–272.

Phillips et al., JMRI: MR Imaging of Ho: YAG Laser Diskectomy with Histologic Correlation, vol. 3 No. 3, May/Jun. 1993.

Bromm et al., Human Neurobiology: Nerve Fibre Discharges, Cerebral Potentials and Sensations Induced by CO2 laser Stimulation, vol.3, (1984) pp. 33–40.

Kolarik et al., Photonucleolysis of Intervertebral Disc and it's Herniation, vol. 51, (1990) pp. 69–71.

Vorwerck et al., Laserblation des Nucleus Pulposus: Optische Eigenschaften von Degeneriertem Bandscheibengewebe im Wellenlangenbereich von 200 bis 2200nm, vol. 151 No. 6, (1989) pp. 725–728.

Wolgin et al., Excimer Ablation of Human Intervertebral Disc at 308 Nanometers, vol. 9, (1989) pp. 124–131.

Davis, Early experience with Laser Disc Decompression, vol. 79 No. 1, (1992) j. Florida M.A.

Quigley et al., Laser Discectomy: Comparison of Systems, vol. 19 No. 3 (1994) pp. 319–322.

Mehta et al., The Treatment of Chronic back Pain: A Preliminary survey of the Effect of Radiofrequency Denervation of the Posterior Vertebral Joints, vol. 34 (1979) pp. 768–775.

Patil et al., Percutaneous Discectomy Using the Electomagnetc Field Focusing Probe: A Feasability Study.

McCulloch et al., CMA Journal: Percutaneous Radiofrequency Lumbar Rhizolysis (rhizotomy), vol. 116, Jan. 8, 1977.

Yonezawa et al., The System and Procedure of Percutaneous Intradiscal Laser Nucleotomy, vol. 15 No. 11 (1990).

Sminia et al., Effects of 434 MHz Microwave Hyperthermia applied to the rat in the region of the cervical Spinal Cord, vol. 3 No. 5 (1987) pp. 441–452.

Sluijter et al., Treatment of Chronic Back and Neck Pain by Percutaneous Therman Lesions, vol. 3 (1981).

* cited by examiner

ELECTROCAUTERIZING TOOL FOR ORTHOPEDIC SHAVE DEVICES

RELATIONSHIP TO COPENDING APPLICATION

This application is a Utility Application which claims priority to Provisional Application No. 60/059,383, entitled Electrocauterizing Sheath for Arthroscopic Shave Device filed on Sep. 19, 1997. This application is related to Utility Application No. 09/034,830, U.S. Pat. No. 6,004,320 entitled Clip on Electrocauterizing Sheath for Orthopedic Shave Devices filed on Mar. 4, 1998; and Utility Application No. 09/034,885, U.S. Pat. No. 6,007,533 entitled Electrocauterizing TIP for Orthopedic Shave Devices filed on Mar. 4, 1998, all of which are incorporated herein by reference.

BACKGROUND OF THE INVENTION

1. Field of the Invention

This invention relates to improved surgical and cauterizing apparatus and methods for their use.

2. Description of Related Art

Arthroscopic surgery is becoming increasingly popular, because it generally does less damage than open procedures, produces less scarring in and around joints, and results in faster healing and return of the patient to full productivity.

Nevertheless, arthroscopic surgery has its limitations. The surgeon must operate through a narrow tube formed in the body on which surgery is being carried out, which is awkward. Only one probe can be used at a time for many operations. Often the viewing camera is positioned at an angle different from the surgeon's normal gaze. This contrasts with "open surgery" where the surgeon has relative ease of viewing the surgical site and can freely move both hands.

Occasionally, during the performance of an arthroscopic or similar minimally invasive procedure, a surgeon will penetrate a vessel within the surgical site. At this point, the surgeon may desire to cauterize the vessel.

One way of cauterizing the vessel is the use of radio frequency (RF) energy, as described in U.S. Pat. No. 5,100,402 to Fan. Such RF methods offer a quick and relatively easy way of cauterizing penetrated vessels. However, use of current RF cauterizing devices usually requires the surgeon to withdraw the surgical tool being used at the time, and insert a tool for cauterizing the penetrated vessel. This switching of the tools is usually required because of the space limitations involved in arthroscopic surgery.

This switching of tools during surgery can be time consuming, awkward, and potentially dangerous to the patient. Additionally, there is the danger of not being able to locate the penetrated vessel. Therefore, there is the need for an improved surgical apparatus and cutting and cauterizing device and methods for using the apparatus and device to avoid the above-mentioned problems.

SUMMARY OF THE INVENTION

In one aspect, the invention relates to a surgical apparatus, comprising a surgical instrument including a housing and a cannula, and the cannula attached at a proximal end to the housing and defining at a distal end thereof an opening and the housing containing a drive interface; and a surgical tool including a shaft and a tip, and the tip located in the opening, and the shaft contained within the cannula and the shaft mechanically and electrically coupled at a distal end to the tip, and at a proximal end, to the drive interface and an electrical interface, and the drive interface producing a surgical motion of the tip, and the electrical interface producing a cauterizing action of the tip.

In another aspect, the invention relates to a cutting and cauterizing device for connection to a surgical instrument, and the surgical instrument including a drive interface and a first interconnector, and the cutting and cauterizing device comprising a cannula defining at a distal end thereof an opening; a second interconnector, suitable for switchably coupling to a power supply, and the second interconnector located at the proximal end of the cannula and shaped to couple to the first interconnector; and a surgical tool including a shaft and a tip, and the tip located in the opening, and the shaft contained within the canula, and the shaft coupled at a distal end to the tip and at a proximal end mechanically coupled to the drive interface to permit a surgical motion of the tip, and electrically coupled to the second interconnector to permit a cauterizing action of the tip.

In yet another aspect, the invention relates to methods of performing surgical procedures, using the surgical apparatus or the cutting and cauterizing device in the course of performing the surgical procedure.

DETAILED DESCRIPTION OF THE INVENTION

Figure 1A:
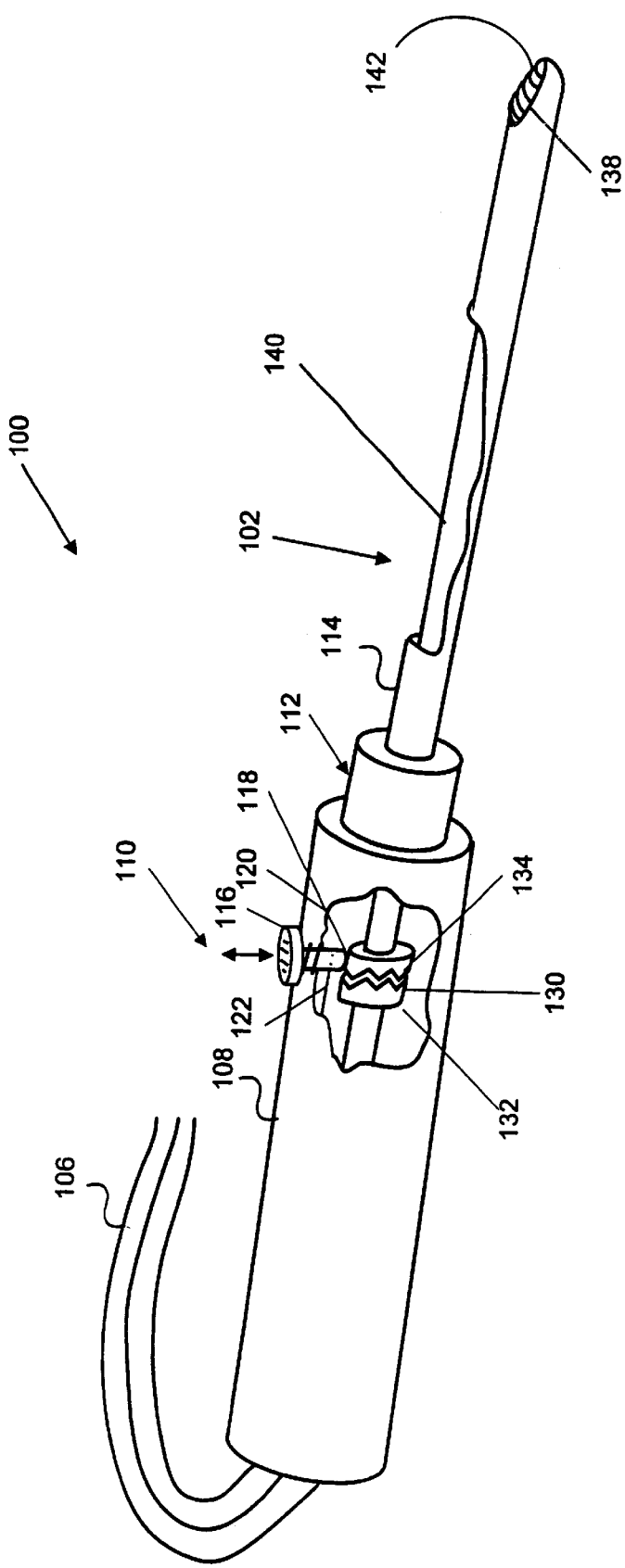
FIG. 1A is an isometric view of an embodiment of the claimed surgical instrument.

FIG. 1A shows an isometric view of surgical apparatus 100, including surgical tool 102 and surgical instrument 110. Surgical instrument 110 includes housing 108, power cord 106, and interconnector 112. Housing 108 also includes push switch 116, electrical contact 118, spring 120, wire 122, and drive interface 132. Surgical tool 102 includes drive coupling 130, commutator 134, shaft 140, and tip 142. Surgical tool 102 additionally includes cannula 114, and opening 138.

Surgical instrument 110 includes housing 108, attached at a distal end, via interconnector 112, to a proximal end of cannula 114. The distal end of cannula 114 defines an opening 138. Shaft 140 is contained within cannula 114. Tip 142 is at the distal end of shaft 140 and protrudes through opening 138 at distal end of cannula 114. At the proximal end of shaft 140 are located commutator 134, and drive coupling 130. Located within housing 108 is drive interface 132, located adjacent to drive coupling 130. Power cord 106 enters housing 108 at a proximal end. Power cord 106 electrically couples to electrical contact 118 via wire 122. Push switch 116 is located on housing 108. The push switch 116 may compose a first electrical member. The push switch is connected to electrical contact 118. The electrical contact is aligned with commutator 134. The commutator 134 may compose a second electrical member. Spring 120 biases electrical contact 118 away from the commutator.

The electrical contact 118 can include a brush. The commutator 134 can include a disk.

In operation, drive interface 132 engages drive coupling 130 to produce surgical motion of tip 142, which is transmitted by shaft 140. Push switch 116 may be depressed against spring 120 to create an electrical contact between electrical contact 118 and commutator 134. This closes a circuit between the power supplied through power cord 106 and wire 122 through shaft 140 to tip 142, thereby producing a cauterizing action at the tip 142.

It should be noted that the surgical motion in any of the embodiments of this invention, can be, for example, rotary, reciprocal, rotary-reciprocal, etc. The shaft and cannula can be straight, or can include an arcuate section. In those instances where the surgical tool contains an arcuate section, the shaft may contain a flexible section to accommodate the motion of the shaft.

Figure 1B:
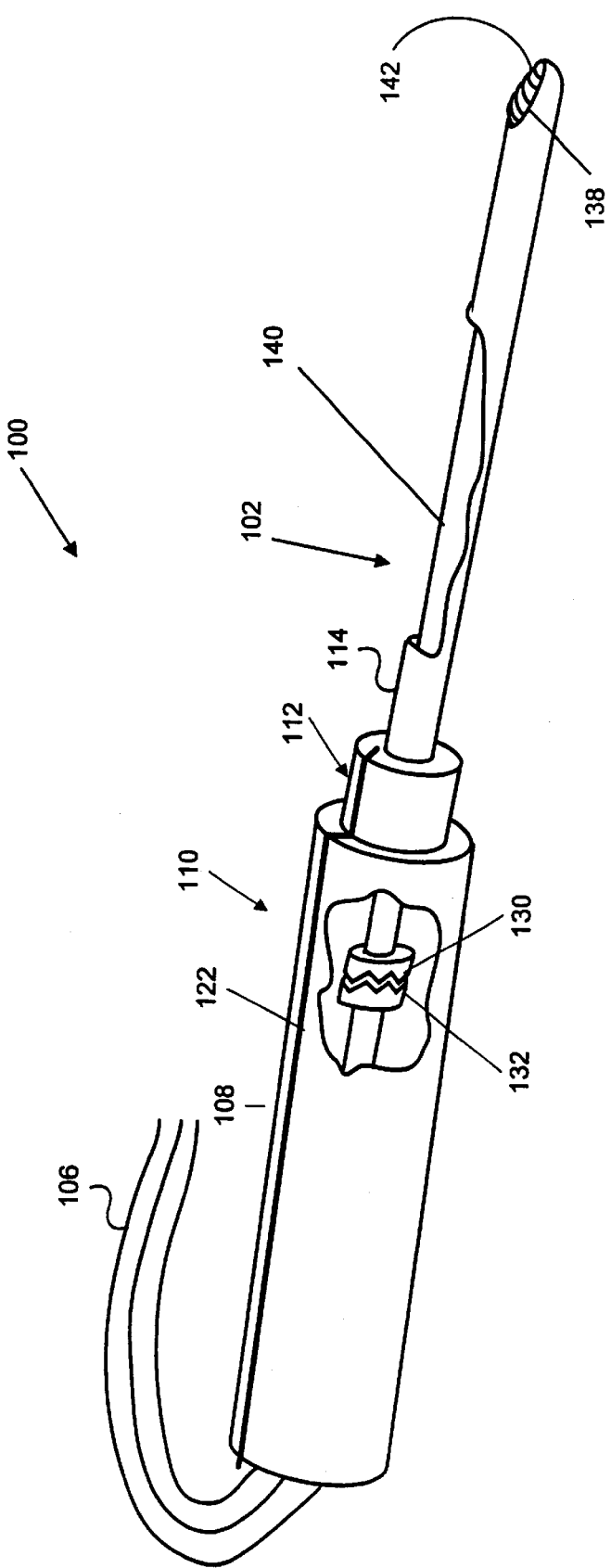
FIG. 1B is an isometric view of another embodiment of the claimed surgical instrument, showing a retrofitted housing.

FIG. 1B shows another isometric view of a different embodiment of the invention, wherein the use of a removable interconnector allows the surgical tool to be removed from the housing. FIG. 1B shows surgical apparatus 100, which includes surgical instrument 110, and surgical tool 102. Surgical instrument 110 includes housing 108. Surgical tool 102 includes drive coupling 130, interconnector 112, shaft 140, tip 142, cannula 114, and opening 138. Interconnector 112 includes wire 122. Housing 108 includes power cord 106, and drive interface 132.

Cannula 114 is connected at a proximal end to interconnector 112. The interconnector may be removably connected to a distal end of housing 108. Distal end of cannula 114 defines opening 138. Shaft 140 is contained within the cannula and has at its distal end tip 142, which protrudes through opening 138 in the cannula. The proximal end of the shaft extends into the housing. Drive coupling 130 is affixed to the proximal end of the shaft. The drive coupling and the proximal end of the shaft are contained within the housing. Power cord 106 is connected to a proximal end of the housing. Also within the housing is a drive interface 132, positioned adjacent to the drive coupling. Wire 122 is removably attached to the exterior of the housing. The wire is used to connect a power supply to the interconnector.

In operation, drive interface 132 is energized by power cord 106, and engages drive coupling 130 to produce a surgical motion of tip 142, which is transmitted via shaft 140. Electrical power is supplied via wire 122 to interconnector 112 to tip 142, via shaft 140, so as to produce a cauterizing action at tip 142. The design of the interconnector allows the surgical tool to be removed from the housing.

Figure 2A:
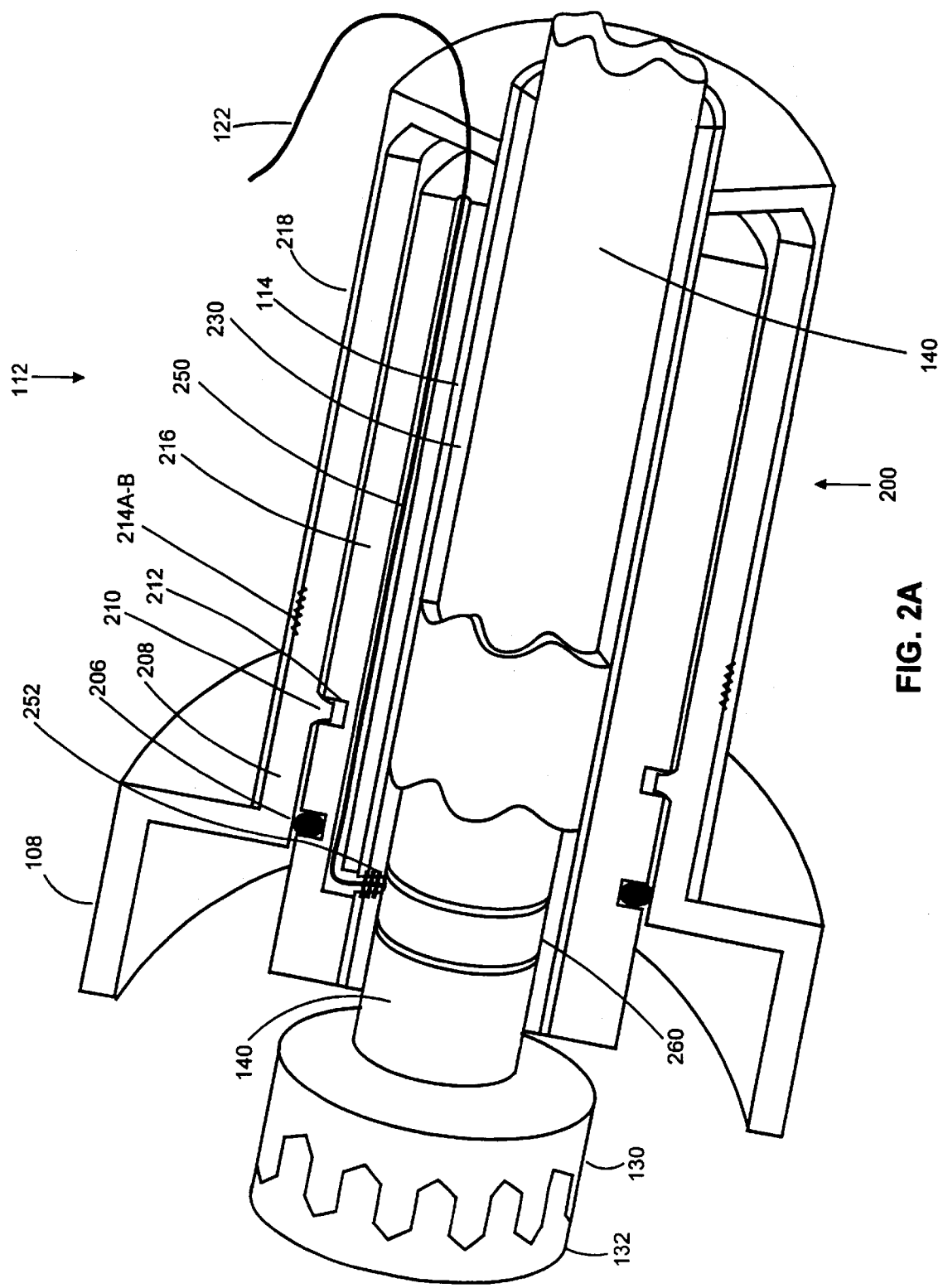
FIG. 2A is a cross section of the embodiment shown in FIG. 1B, having a generally conducting shaft.
Figure 2B:
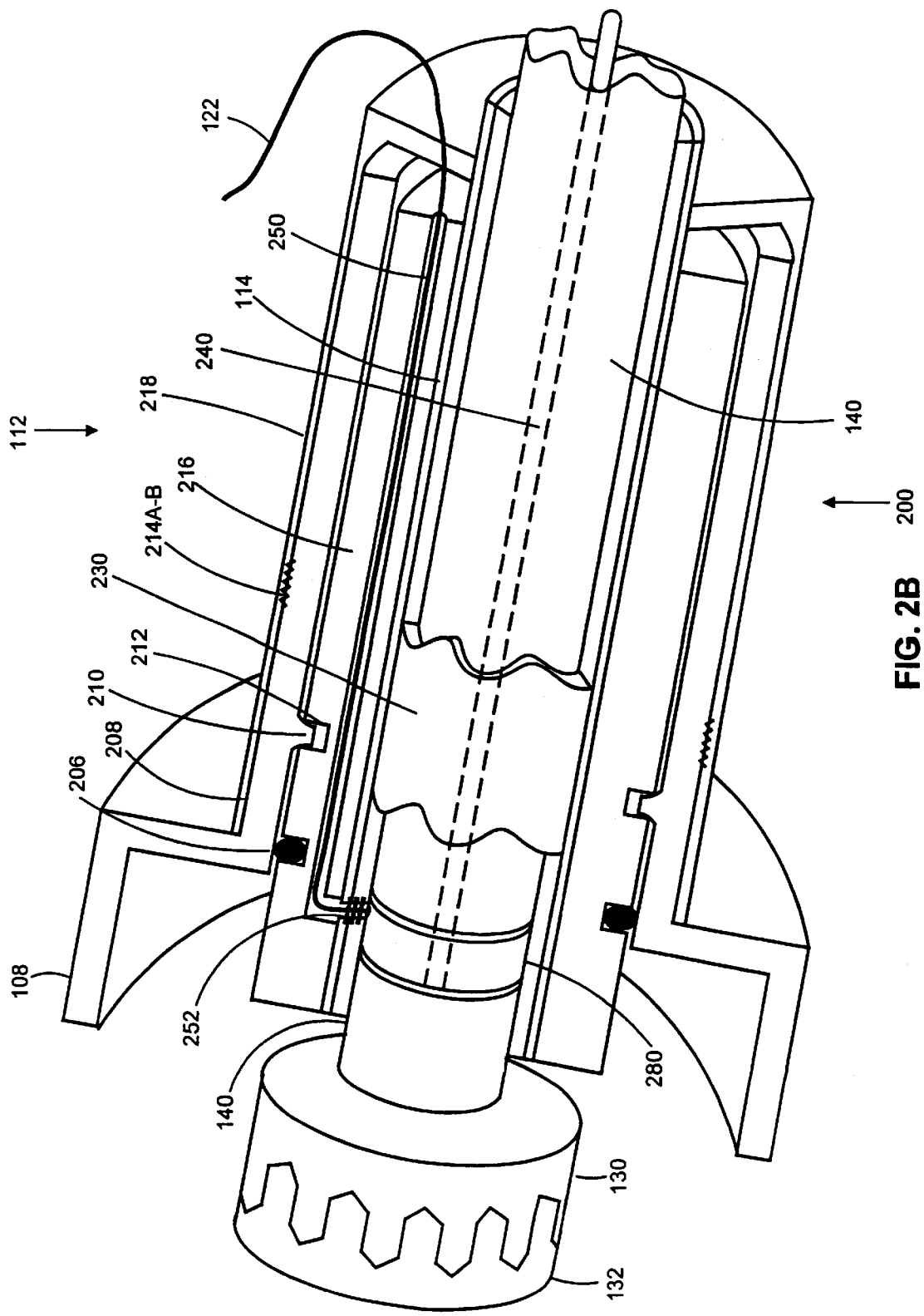
FIG. 2B is a cross section of the embodiment shown in FIG. 1B, having a generally insulating shaft.

FIGS. 2A–B are enlarged cross-sectional views of interconnector 112. In FIGS. 2A–B, an embodiment of the invention is shown in which the interconnector is removable from housing 108 as shown in FIG. 1B. FIG. 2A shows such an embodiment, where shaft 140 is generally conducting, while FIG. 2B shows such an embodiment where the shaft is generally non-conducting, but has an interior conductor 240.

FIG. 2A shows surgical apparatus 200, which includes housing 108, and interconnector 112. The housing includes extended housing portion 208. Interconnector 112 includes outer O-ring seal 206, locking member 216, interconnector conductor 250, electrical connector 252, and locking ring 218. Also shown are cannula 114, inner alignment piece 230, and shaft 140, drive coupling 130, commutator 260. Furthermore, drive interface 132 is shown.

Shaft 140 is contained within cannula 114, and kept separate from the cannula by inner alignment piece 230. The cannula, inner alignment piece, and shaft are connected at their proximal ends to housing 108 via interconnector 112. Interconnector 112 serves to locate the shaft, inner alignment piece, and cannula. Interconnector 112 includes locking member 216 which is shaped so as to secure the cannula within extended housing portion 208. The locking member also has a notch 212, which is located opposite a detent 210 located on an interior surface of the extended housing portion. The locking member additionally includes outer o-ring seal 206, located between the locking member exterior surface and the extended housing portion interior surface. The extended housing portion includes exterior threads 214A, located so as to be opposite interior threads 214B, which are located on locking ring 218. Located at a proximal end of shaft 140 are commutator 260 and drive coupling 130. Wire 122 delivers power to commutator 260 via interconnector conductor 250, and electrical connector 252. The electrical connector is located such that it is in electrical connector with commutator 260.

In operation, interconnector 112 serves to attach inner alignment piece 230, shaft 140 and cannula 114 to the housing. The inner alignment piece serves to locate the shaft within the cannula, and also serves as a bearing for the shaft. Locking member 216 serves to locate the inner alignment piece within extended housing portion 208 through the engagement of notch 212 on the locking member and detent 210 on the interior of the extended housing portion. Locking ring 218 serves to secure the locking member, together with the cannula, inner alignment piece and shaft, within the extended housing portion. The locking ring accomplishes this via the cooperative action of its interior threads 214B and exterior threads 214A, which are located on the exterior surface of the extended housing portion. Drive coupling 130 serves to impart a surgical motion to shaft 140. Outer O-ring seal 206 serves to prevent transmission of body fluids that may be present at the distal end of the shaft through to the housing. Electrical power is provided via wire 122, to commutator 260. Commutator 260 is electrically coupled to distal end of shaft 140, thus producing a cauterizing effect at the distal end of the shaft. FIG. 2B shows a cross section of another embodiment of surgical apparatus 200, which shows a generally insulating shaft including an interior conductor 240. The elements, their arrangement and function are identical to those described above in FIG. 2A with the following differences. The interior conductor is located within shaft 140. The shaft is generally insulating. The interior conductor electrically couples commutator 280 to the distal end of the shaft, thereby permitting a cauterizing action at the distal end of the shaft.

Figure 3A:
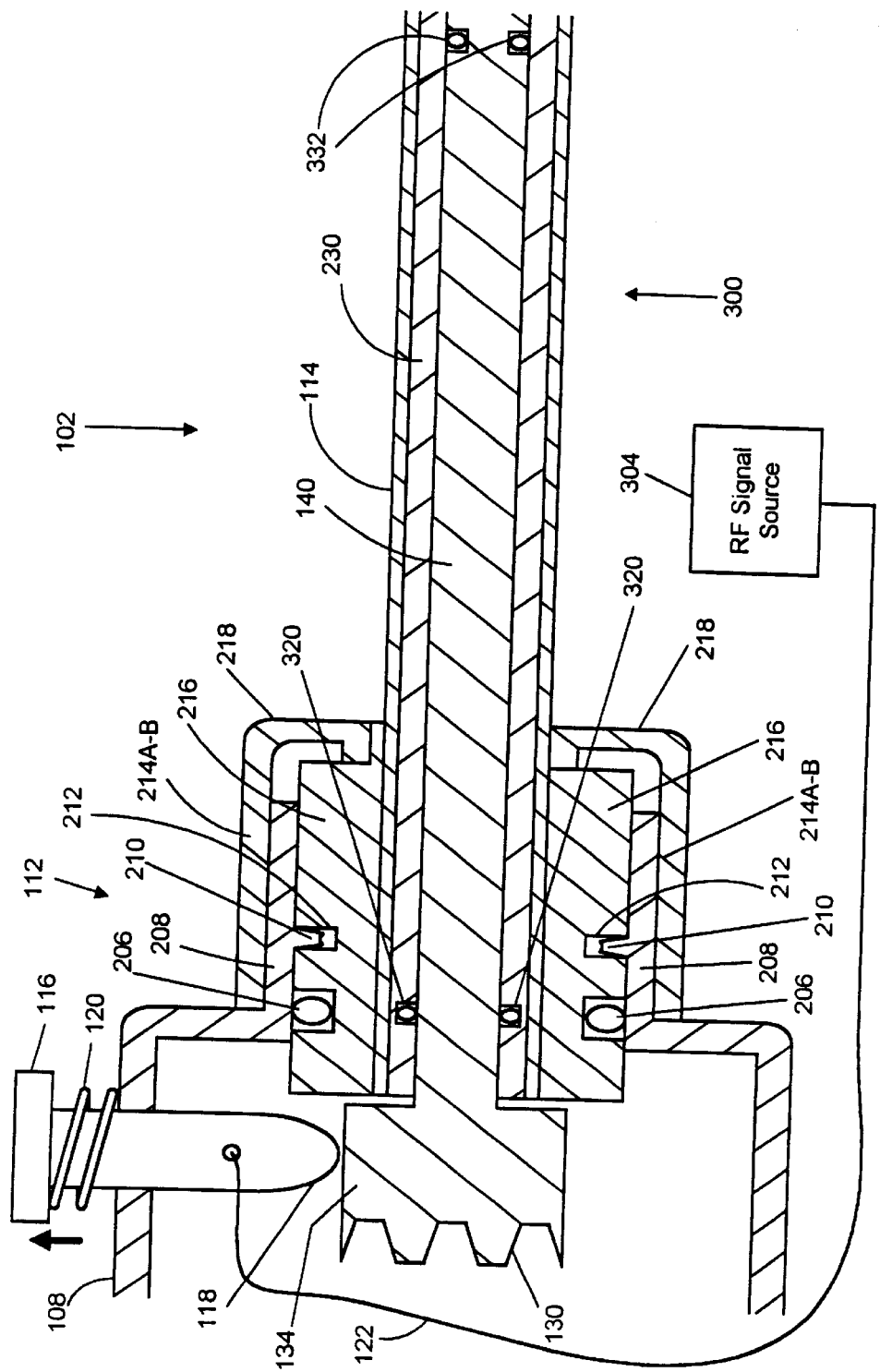
FIGS. 3A–D are cross-sectional views of other embodiments of the surgical instrument, showing details of different interconnector arrangements.
Figure 3B:
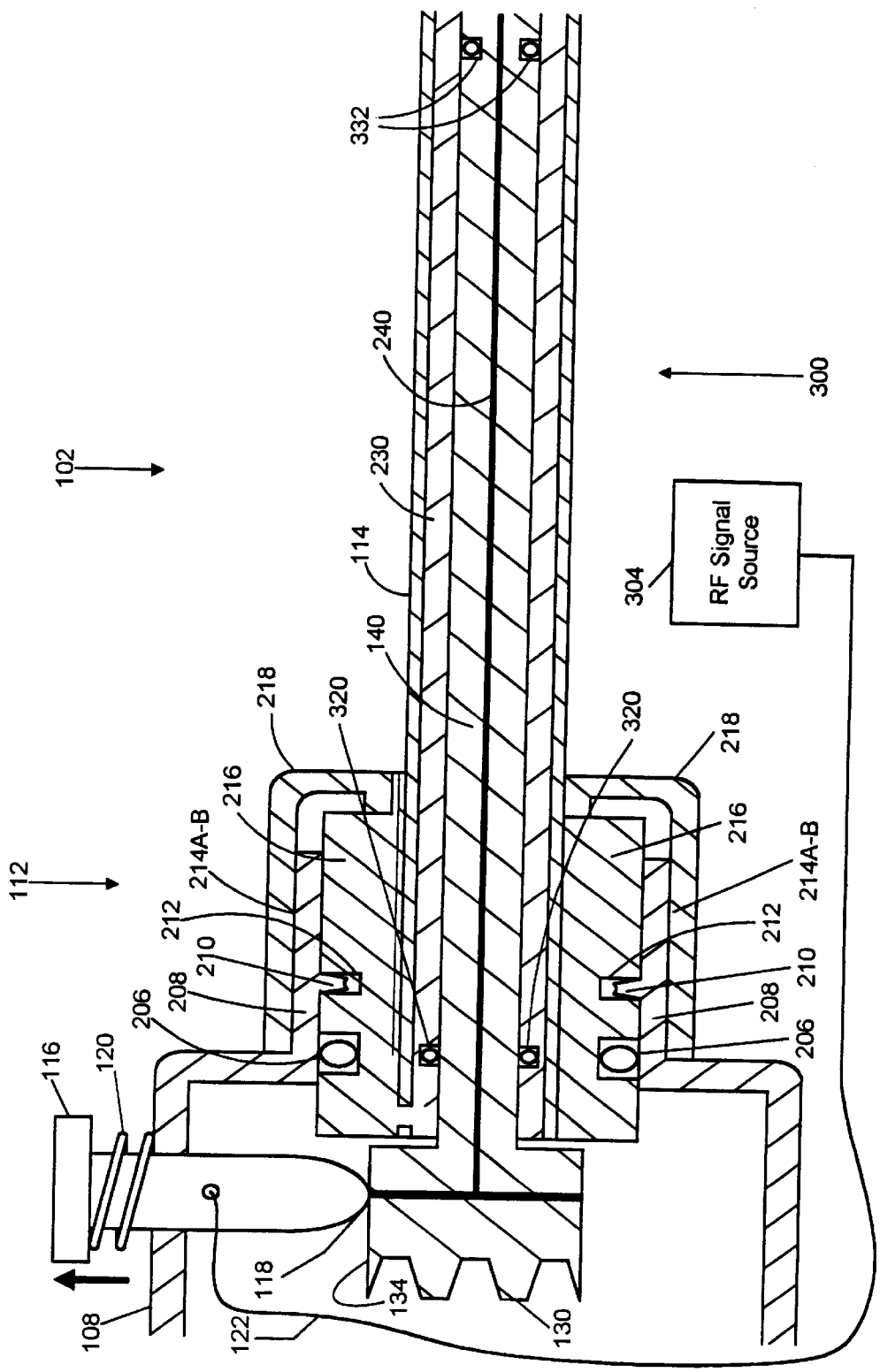

FIGS. 3A–D are enlarged cross-sectional views of interconnector 112. In FIGS. 3A–D, an embodiment of the invention is shown in which surgical tool 102 and the interconnector are removable from housing 108. FIGS. 3A–B show cross-sectional views of the surgical apparatus shown in FIG. 1A. In the cross section views shown in FIGS. 3A–B, the electrical interface is integrated into the housing, rather than being located within the interconnector. FIGS.

Figure 3C:
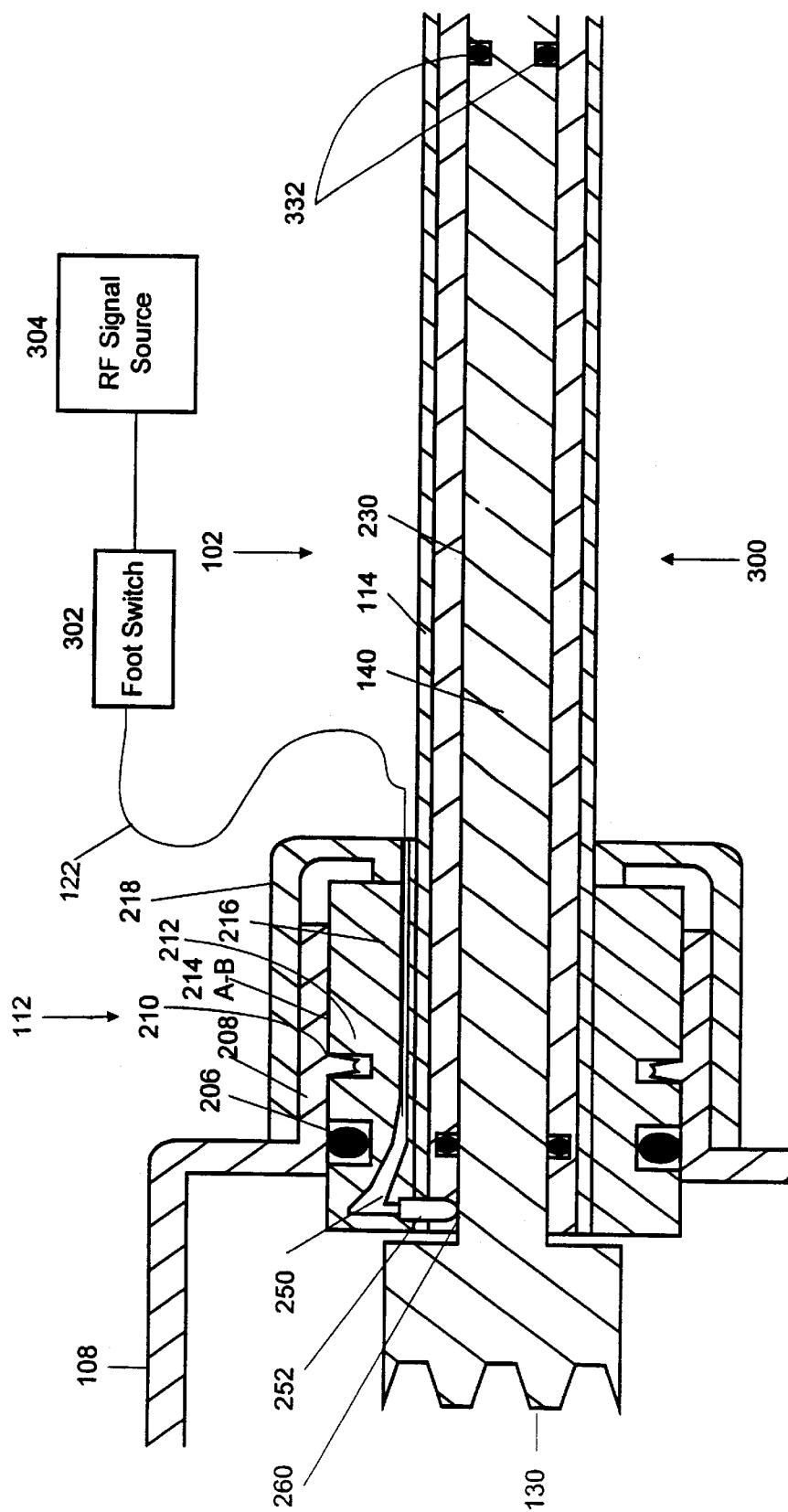
Figure 3D:
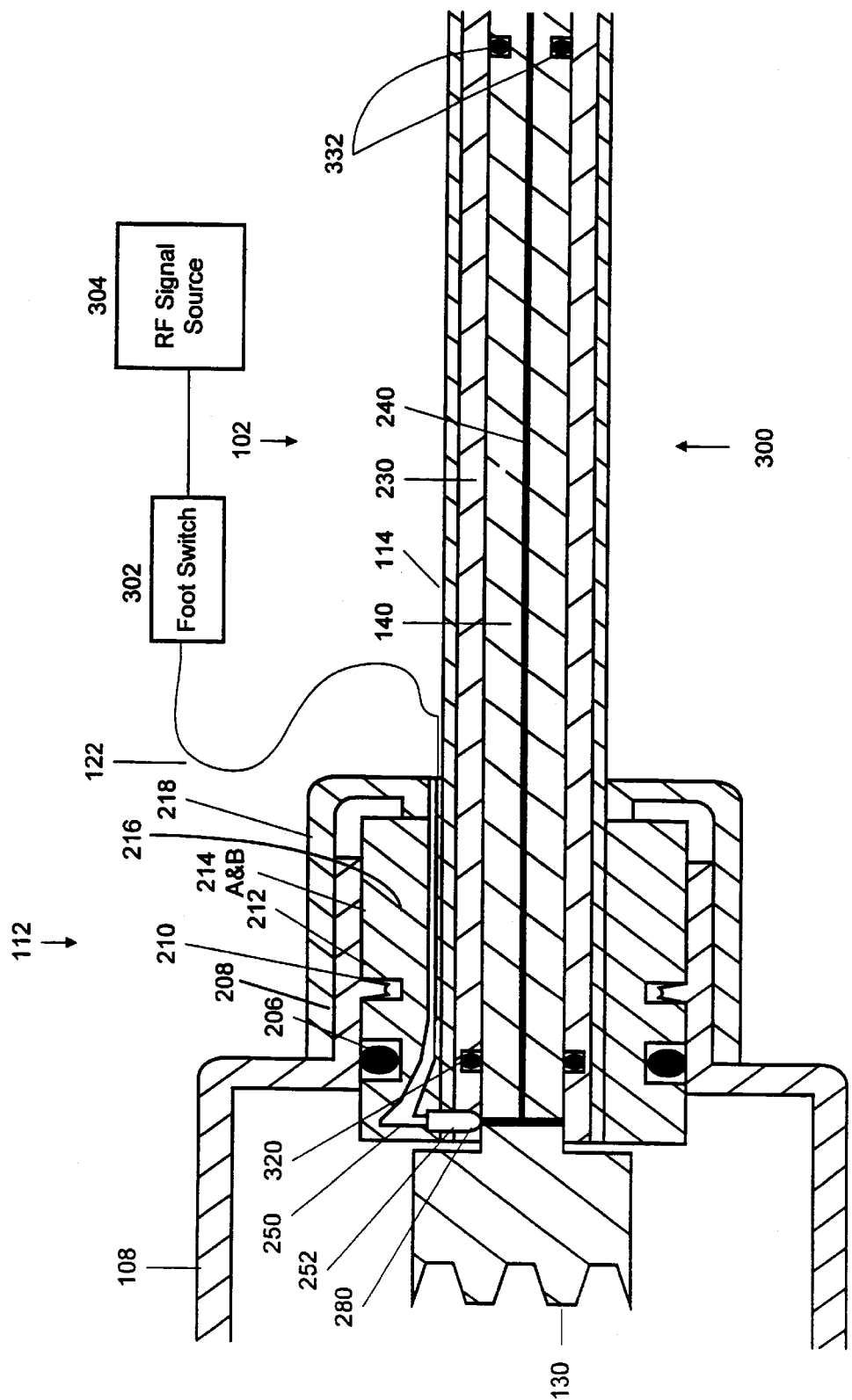

3A–B, show an electrical interface between the tool and power supply, located in the housing. FIGS. 3C–D are cross-sectional views of the apparatus shown in FIG. 1B, in which the electrical interface is integrated into the interconnector, rather than being located within the interconnector. FIGS. 3C–D show an electrical interface, between the surgical tool and power supply, located in the interconnector.

FIG. 3A shows surgical apparatus 300, which includes housing 108, interconnector 112, and surgical tool 102. Also shown is RF signal source 304. The housing includes extended housing portion 208, push switch 116, spring 120, and electrical contact 118. Interconnector 112 includes outer O-ring seal 206, locking member 216, and locking ring 218. Surgical tool 102 includes cannula 114, inner alignment piece 230, shaft 140, drive coupling 130, commutator 134, inner O-ring seal 320, and distal O-ring seal 332.

Shaft 140 is contained within cannula 114, and kept separate from the cannula by inner alignment piece 230. Distal O-ring seal 332 is located within a retaining groove at a distal end of shaft 140, and is in contact with the interior of the inner alignment piece. The cannula, inner alignment piece, and shaft are connected at their proximal ends to housing 108 via interconnector 112. The inner alignment piece locates inner o-ring seal 320 between the inner alignment piece and the shaft near the proximal end of the inner alignment piece and the shaft. Interconnector 112 serves to locate the shaft, inner alignment piece, and cannula. Interconnector 112 includes locking member 216 which is shaped so as to secure the cannula within extended housing portion 208. The locking member also has a notch 212, which is located opposite a detent 210 located on an interior surface of the extended housing portion. The locking member additionally includes outer o-ring seal 206, located between the locking member exterior surface and the extended housing portion interior surface. The extended housing portion includes exterior threads 214A, located so as to be opposite interior threads 214B, which are located on locking ring 218. Located at a proximal end of shaft 140 are commutator 134 and drive coupling 130. RF signal source 304 is electrically coupled via wire 122 which is coupled in turn with electrical contact 118, via push switch 116. The electrical contact is located such that it is in removable contact with commutator 134. Push switch 116, which is spring biased by spring 120, is located on an exterior surface of the housing.

In operation, interconnector 112 serves to attach inner alignment piece 230, shaft 140 and cannula 114 to the housing. The inner alignment piece serves to locate the shaft within the cannula, and also serves as a bearing for the shaft. Locking member 216 serves to locate the inner alignment piece within extended housing portion 208 through the engagement of notch 212 on the locking member and detent 210 on the interior of the extended housing portion. Locking ring 218 serves to secure the locking member, and thus the whole of surgical tool 102, within the extended housing portion. The locking ring accomplishes this via the cooperative action of its interior threads 214B and exterior threads 214A, which are located on the exterior surface of the extended housing portion. Drive coupling 130 serves to impart a surgical motion to shaft 140. Distal O-ring seal 332, outer O-ring seal 206 and inner O-ring seal 320 serve to prevent transmission of body fluids that may be present at the distal end of the shaft through to the housing. RF signal source 304 serves to provide power via wire 122, and electrical contact 118 to commutator 134. Commutator 134 is electrically coupled to distal end of shaft 140, thus producing a cauterizing effect at the distal end of the shaft.

The electrical circuit is closed when push switch 116 is depressed against spring 120 to bring electrical contact 118 into electrical contact with commutator 134. FIG. 3B shows a cross section of another embodiment of surgical apparatus 300, which shows a generally insulating shaft including an interior conductor 240. The elements, their arrangement and function are identical to those described above in FIG. 3A with the following differences. The interior conductor is located within shaft 140, and electrically couples commutator 134 to the distal end of the shaft, thereby permitting a cauterizing action at the distal end of the shaft.

FIGS. 3C–D show an electrical interface, between the surgical tool and power supply, located in the interconnector. In particular, FIGS. 3C–D show embodiments of the invention that may include existing housings, thus allowing retrofitting of such housings in the practice of the invention. Such retrofitting is expressly and generally within the scope of the invention. FIG. 3C shows surgical apparatus 300, which includes housing 108, interconnector 112, and surgical tool 102. Also shown are foot switch 302, and RF signal source 304. The housing includes extended housing portion 208. Interconnector 112 includes outer O-ring seal 206, locking member 216, interconnector conductor 250, electrical connector 252, and locking ring 218. Surgical tool 102 includes cannula 114, inner alignment piece 230, shaft 140, drive coupling 130, commutator 260, inner O-ring seal 320, and distal O-ring seal 332.

Shaft 140 is contained within cannula 114, and kept separate from the cannula by inner alignment piece 230. Distal O-ring seal 332 is located within a retaining groove at a distal end of shaft 140, and is in contact with the interior of the inner alignment piece. The cannula, inner alignment piece, and shaft are connected at their proximal ends to housing 108 via interconnector 112. The inner alignment piece locates inner o-ring seal 320 between the inner alignment piece and the shaft near the proximal end of the inner alignment piece and the shaft. Interconnector 112 serves to locate the shaft, inner alignment piece, and cannula. Interconnector 112 includes locking member 216 which is shaped so as to secure the cannula within extended housing portion 208. The locking member also has a notch 212, which is located opposite a detent 210 located on an interior surface of the extended housing portion. The locking member additionally includes outer o-ring seal 206, located between the locking member exterior surface and the extended housing portion interior surface. The extended housing portion includes exterior threads 214A, located so as to be opposite interior threads 214B, which are located on locking ring 218. Located at a proximal end of shaft 140 are commutator 134 and drive coupling 130. RF signal source 304 is electrically coupled to commutator 260 via foot switch 302, wire 122, interconnector conductor 250, and electrical connector 252. Commutator 260 is electrically coupled to distal end of shaft 140.

In operation, interconnector 112 serves to attach inner alignment piece 230, shaft 140 and cannula 114 to the housing. The inner alignment piece serves to locate the shaft within the cannula, and also serves as a bearing for the shaft. Locking member 216 serves to locate the inner alignment piece within extended housing portion 208 through the engagement of notch 212 on the locking member and detent 210 on the interior of the extended housing portion. Locking ring 218 serves to secure the locking member, and thus the whole of surgical tool 102, within the extended housing portion. The locking ring accomplishes this via the cooperative action of its interior threads 214B and exterior threads 214A, which are located on the exterior surface of the extended housing portion. Drive coupling 130 serves to transfer a surgical motion from a drive interface (not shown) to shaft 140. Distal O-ring seal 332, outer O-ring seal 206 and inner O-ring seal 320 serve to prevent transmission of body fluids that may be present at the distal end of the shaft through to the housing. RF signal source 304 serves to provide power to commutator 260 via foot switch 302, wire 122, interconnector conductor 250, and electrical connector 252. Commutator 260 is electrically coupled to distal end of shaft 140, thus producing a cauterizing effect at the distal end of the shaft.

FIG. 3D shows a cross section of another embodiment of surgical apparatus 300, which shows a generally insulating shaft including an interior conductor 240. The elements, their arrangement and function are identical to those described above in FIG. 3A with the following differences. The interior conductor is located within generally insulating shaft 140, and electrically couples commutator 280 to the distal end of the shaft, thereby permitting a cauterizing action at the distal end of the shaft.

Figure 4A:
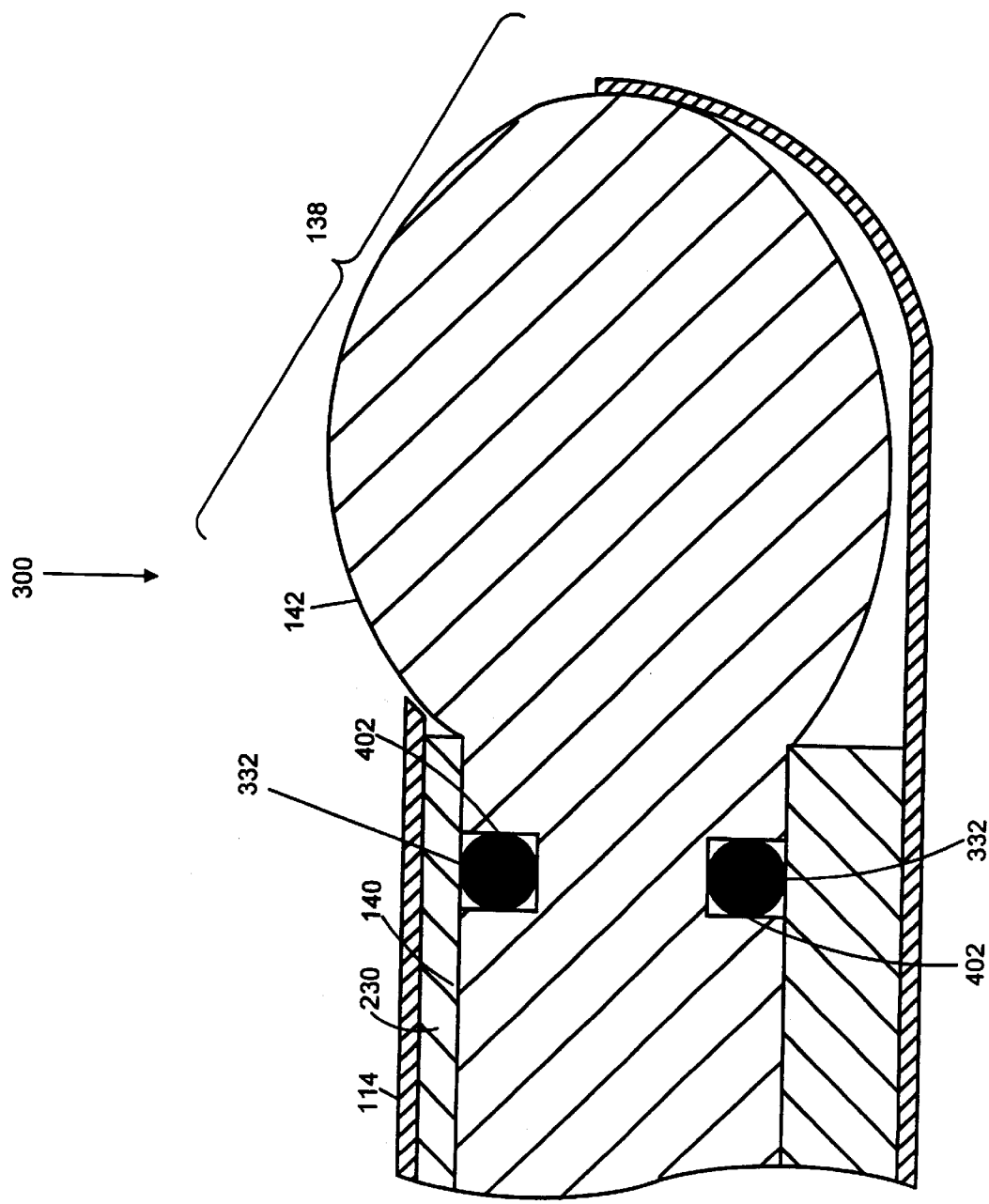
FIGS. 4A–B are cross-sectional views of embodiments of the surgical instrument, emphasizing different distal seal arrangements.

FIG. 4A shows a cross section of the distal end of a surgical apparatus according to the invention, featuring details of tip 142, including conducting and non-conducting portions, and a distal O-ring seal arrangement. Surgical apparatus 300 includes cannula 114, inner alignment piece 230, shaft 140, tip 142, distal O-ring seal 332, distal O-ring seat 402, and opening 138.

Shaft 140 is contained within inner alignment piece 230 which in turn is contained within cannula 114. Cannula 114, at its distal end, defines opening 138. The distal end of the shaft is attached to tip 142, which is located within the opening. The distal end of the shaft also includes distal O-ring seats 402. Distal O-ring seal 332 is located within the distal O-ring seat and is in contact with the interior surface of the inner alignment piece.

In operation surgical motion that is imparted to shaft 140 is thereby transmitted to tip 142. In addition, electrical power delivered to shaft 140 produces a cauterizing effect at tip 142. Inner alignment piece 230 serves to align shaft 140 within cannula 114, and also serves as a bearing surface for shaft 140. Together the shaft, inner alignment piece, and distal O-ring seat 402, and distal O-ring seal 332 serve to produce a seal that prevents transmission of body fluids that may be present at opening 138 from being transmitted along the interface between the inner alignment piece and the shaft.

Figure 4B:
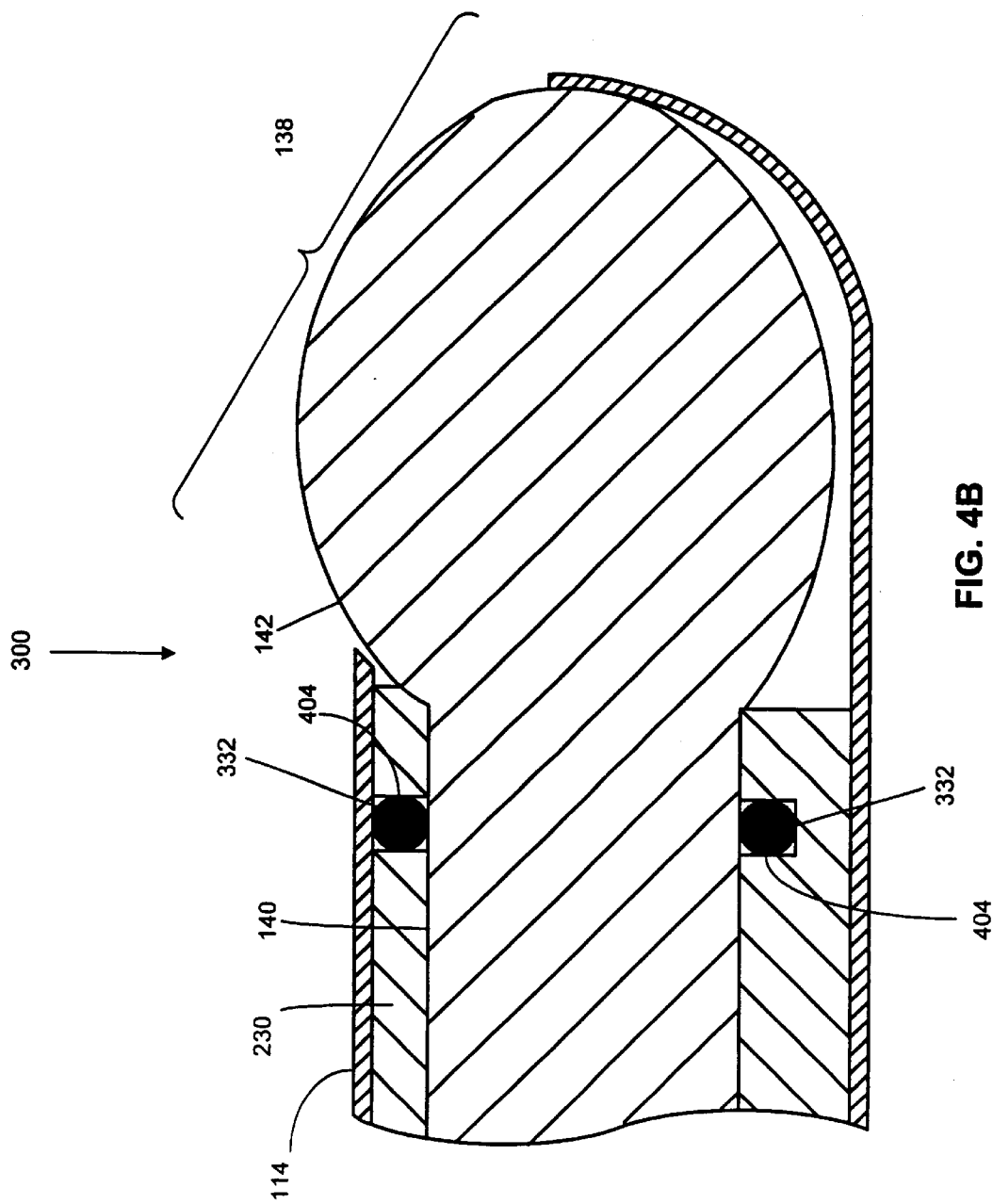

FIG. 4B shows a cross-section of the distal end of a surgical apparatus according to the invention, featuring details of tip 142, including conducting and non-conducting portions, and a distal O-ring seal arrangement. Surgical apparatus 300 includes cannula 114, inner alignment piece 230, shaft 140, tip 142, distal O-ring seal 332, distal O-ring seat 404, and opening 138.

Shaft 140 is contained within inner alignment piece 230 which in turn is contained within cannula 114. Cannula 114, at its distal end, defines opening 138. The distal end of the shaft is attached to tip 142, which is located within the opening. The distal end of the inner alignment piece also includes distal O-ring seat 404. Distal O-ring seal 332 is located within the distal O-ring seat and is in contact with the interior surface of the inner alignment piece.

In operation surgical motion that is imparted to shaft 140 is thereby transmitted to tip 142. In addition, electrical power delivered to shaft 140 produces a cauterizing effect at tip 142. Inner alignment piece 230 serves to align shaft 140 within cannula 114, and also serves as a bearing surface for shaft 140. Together the shaft, inner alignment piece, and distal O-ring seat 404, and distal O-ring seal 332 serve to produce a seal that prevents transmission of body fluids that may be present at opening 138 from being transmitted along the interface between the inner alignment piece and the shaft.

Figure 5A:
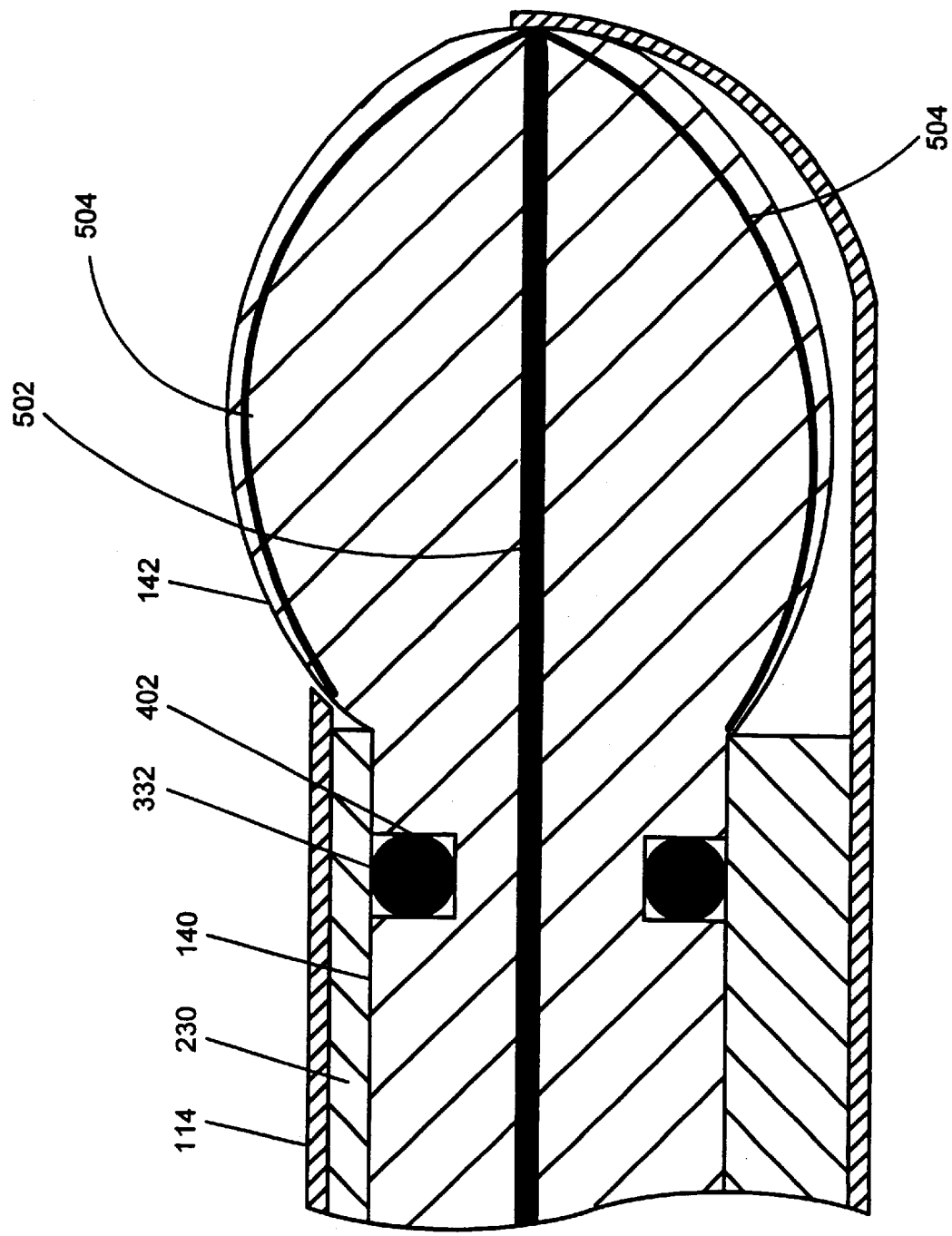
FIGS. 5A–B are cross-sectional views of embodiments of the surgical instrument, emphasizing different distal seal and tip arrangements.

FIG. 5A shows a cross section of the distal end of a surgical apparatus according to the invention, featuring details of generally non-conducting tip 142, and a distal O-ring seal arrangement. Included are cannula 114, inner alignment piece 230, shaft 140, distal O-ring seal 332, and distal O-ring seat 402. Tip 142 includes interior conductor 240, and conducting portion 504.

Shaft 140 is contained within inner alignment piece 230 which in turn is contained within cannula 114. The distal end of the shaft is attached to tip 142. The distal end of the shaft also includes distal O-ring seat 402. Distal O-ring seal 332 is located within the distal o-ring seat, and is in contact with the interior surface of the inner alignment piece. Interior conductor 240 runs through an interior portion of shaft 140 and the tip, and is electrically coupled to a plurality of conducting portions 504 at a single, distal, location. The plurality of conducting portions radiate arcuately along a longitudinal axis of the shaft, and are present at portions of the exterior surface of the tip.

In operation, surgical motion that is imparted to shaft 140 is thereby transmitted to tip 142. In addition, electrical power delivered along interior conductor 240 is transmitted to conducting portion 504, thus producing a cauterizing effect. Inner alignment piece 230 serves to align shaft 140 within cannula 114, and also serves as a bearing surface for shaft 140. Together shaft 140, inner alignment piece 230, distal O-ring seat 404, and distal O-ring seal 332 serve to produce a seal that prevents transmission of body fluids that may be present at the distal end of the shaft from being transmitted along the interface between the inner alignment piece and the shaft.

Figure 5B:
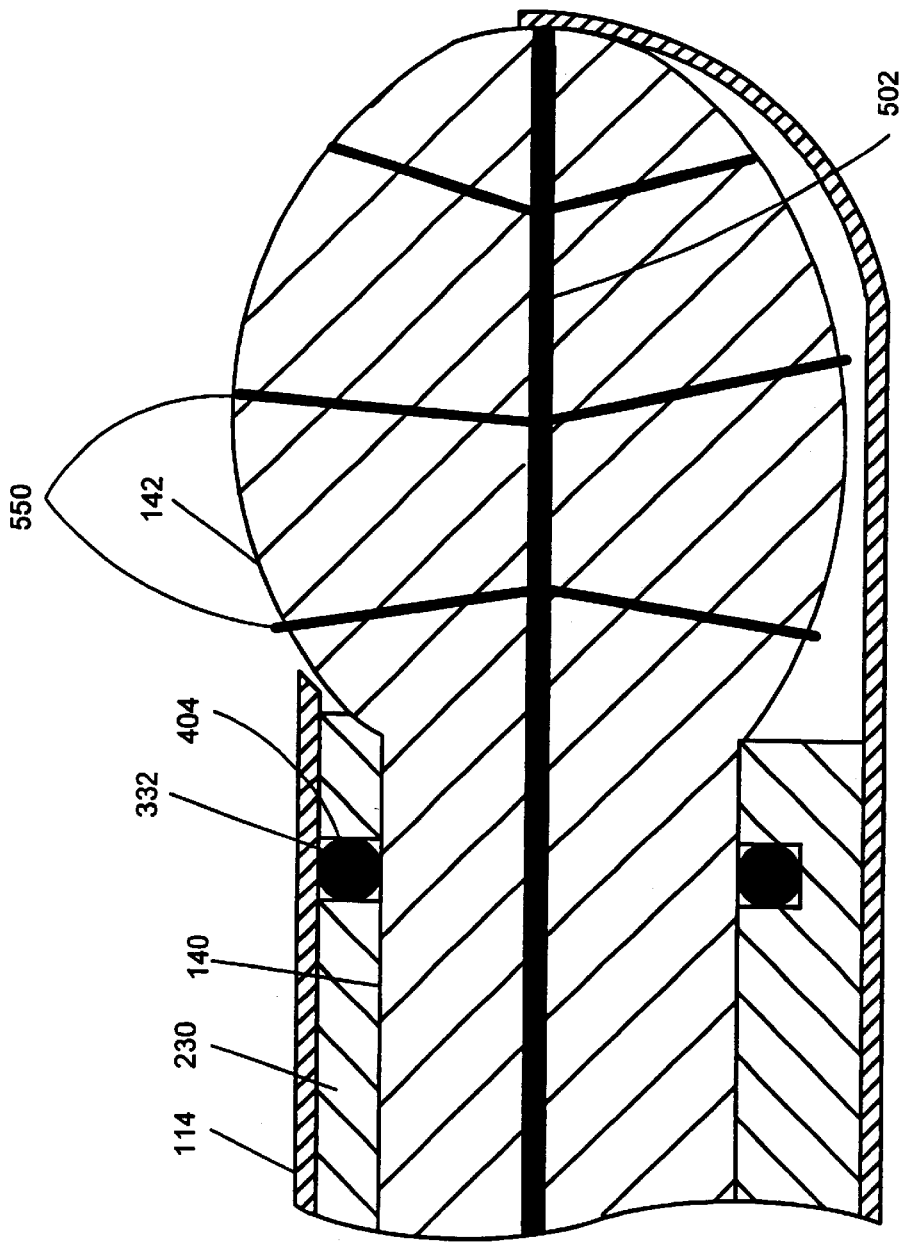

FIG. 5B shows a cross section of the distal end of a surgical apparatus according to the invention, featuring details of another embodiment of a generally non-conducting tip 142, and a distal O-ring seal arrangement. Included are cannula 114, inner alignment piece 230, shaft 140, distal O-ring seal 332, and distal O-ring seat 404. Tip 142 includes interior conductor 240, and conducting portions 550.

Shaft 140 is contained within inner alignment piece 230 which in turn is contained within cannula 114. The distal end of the shaft is attached to tip 142. The distal end of the inner alignment piece also includes distal O-ring seat 404. Distal O-ring seal 332 is located within the distal O-ring seat, and is in contact with the interior surface of the inner alignment piece. Interior conductor 240 runs through an interior portion of shaft 140 and the tip, and is electrically coupled to a plurality of conducting portions 550 at multiple locations within the tip and/or optionally within the distal portion of the shaft. The plurality of conducting portions radiate along a radius extending from a longitudinal axis of the shaft. The conducting portions are present at portions of the exterior surface of the tip.

In operation, surgical motion that is imparted to shaft 140 is thereby transmitted to the tip. In addition, electrical power delivered along interior conductor 240 is transmitted to conducting portions 550, thus producing a cauterizing effect. Inner alignment piece 230 serves to align shaft 140 within cannula 114, and also serves as a bearing surface for shaft 140. Together shaft 140, inner alignment piece 230, distal O-ring seat 404, and distal O-ring seal 332 serve to produce a seal that prevents transmission of body fluids that may be present at the distal end of the shaft from being transmitted along the interface between the inner alignment piece and the shaft.

Figure 6A:
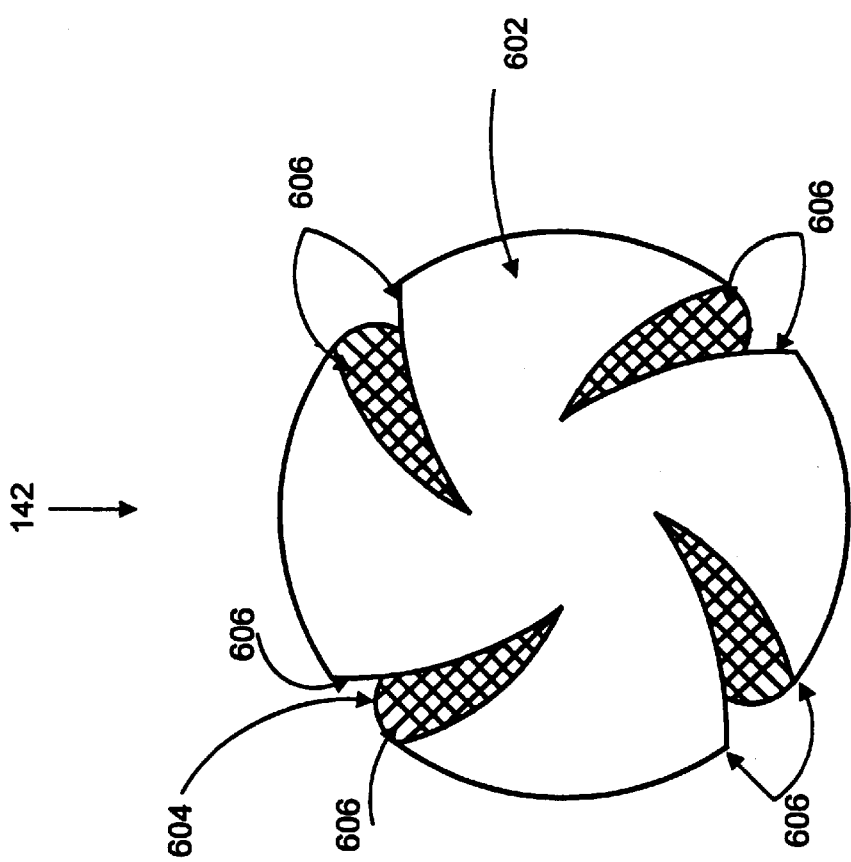
FIGS. 6A–D are end-on views of tips, according to the invention, emphasizing different embodiments of the conducting and non-conducting portions.

FIG. 6A shows an end-on view of a tip shown in cross-sectional view in FIGS. 4A–B, and features various arrangements of the conducting and non-conducting portions. Tip 142 includes conducting portion 602, non-conducting portions 604, and cutting edges 606.

Conducting portion 602 and non-conducting portions 604 are present on the surface of the tip, and have cutting edges 606 in between them.

In operation, tip 142 may be moved in a surgical motion. Additionally, electrical power may be supplied to conducting portions 602, which then permit a cauterizing effect originating at cutting edges 606 to take place. Substantially less or no cauterizing effect takes place at or near non-conductive portions 604.

Figure 6B:
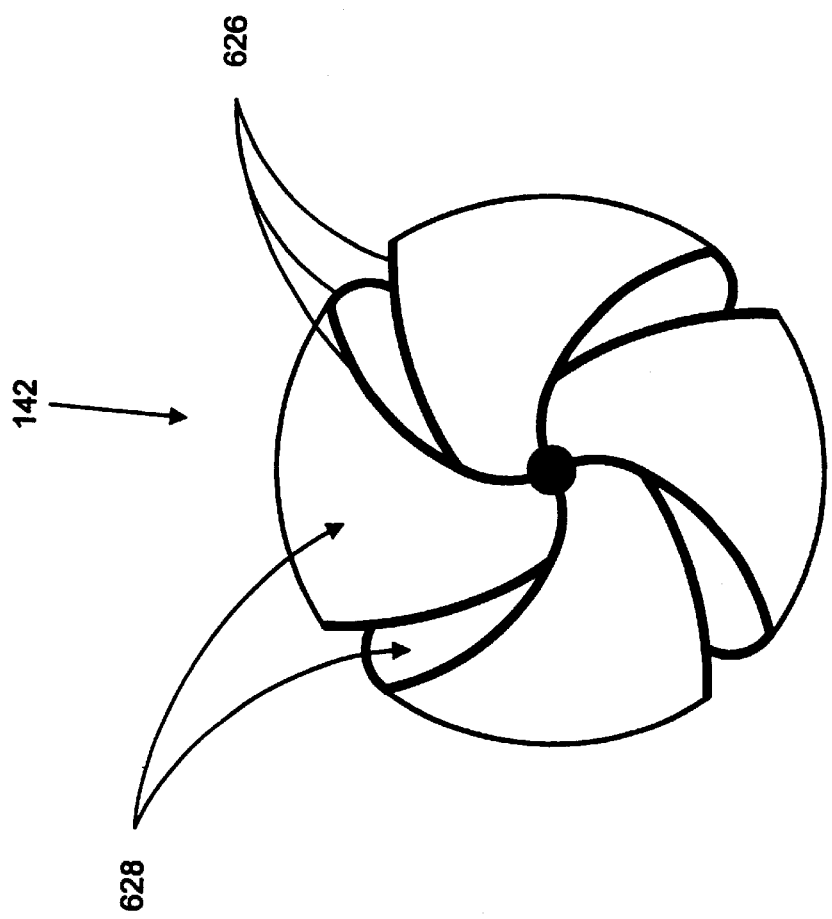

FIG. 6B shows an end-on view of a tip shown in cross-sectional view in FIG. 5A, and features various arrangements of the conducting and non-conducting portions. Tip 142 includes conducting portion 626, and non-conducting portions 628. Conducting portion 626 and non-conducting portions 628 are present on the surface of tip 142.

In operation, tip 142 may be moved in a surgical motion, with conducting portions 626 serving as cutting edges. Additionally, electrical power may be supplied to the conducting portions, which then permit a cauterizing effect to take place.

Figure 6C:
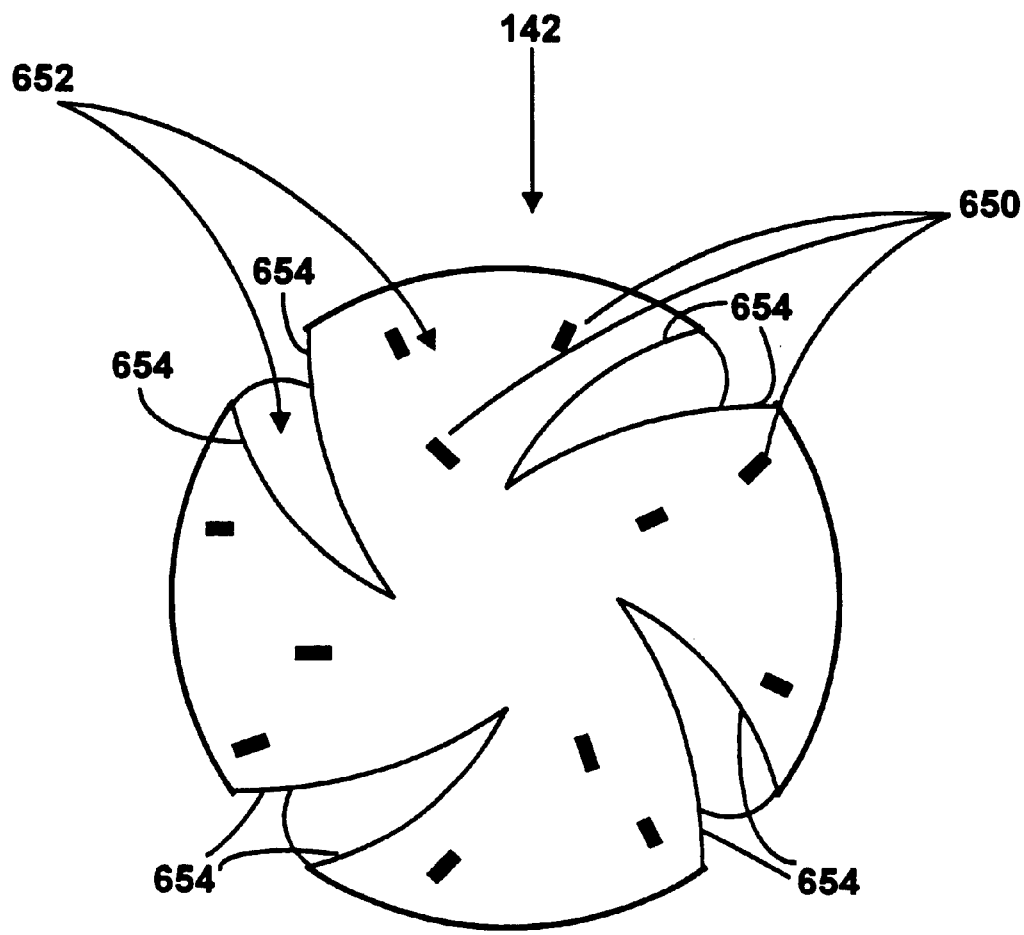

FIG. 6C shows an end-on view of a tip shown in cross-sectional view in FIG. 5B, and features various arrangements of the conducting and non-conducting portions. Tip 142 includes conducting portion 650, non-conducting portions 652, and cutting edges 654.

Conducting portion 650 and non-conducting portions 652 are present on the surface of tip 142. Cutting edges 654 are present on the surface of the tip, and in between the conducting and the non-conducting portions.

In operation, tip 142 may be moved in a surgical motion, utilizing cutting edges 654. Additionally, electrical power may be supplied to conducting portions 650, which then permit a cauterizing effect to take place. Substantially less or no cauterizing effect takes place at or near non-conductive portions 652.

Figure 6D:
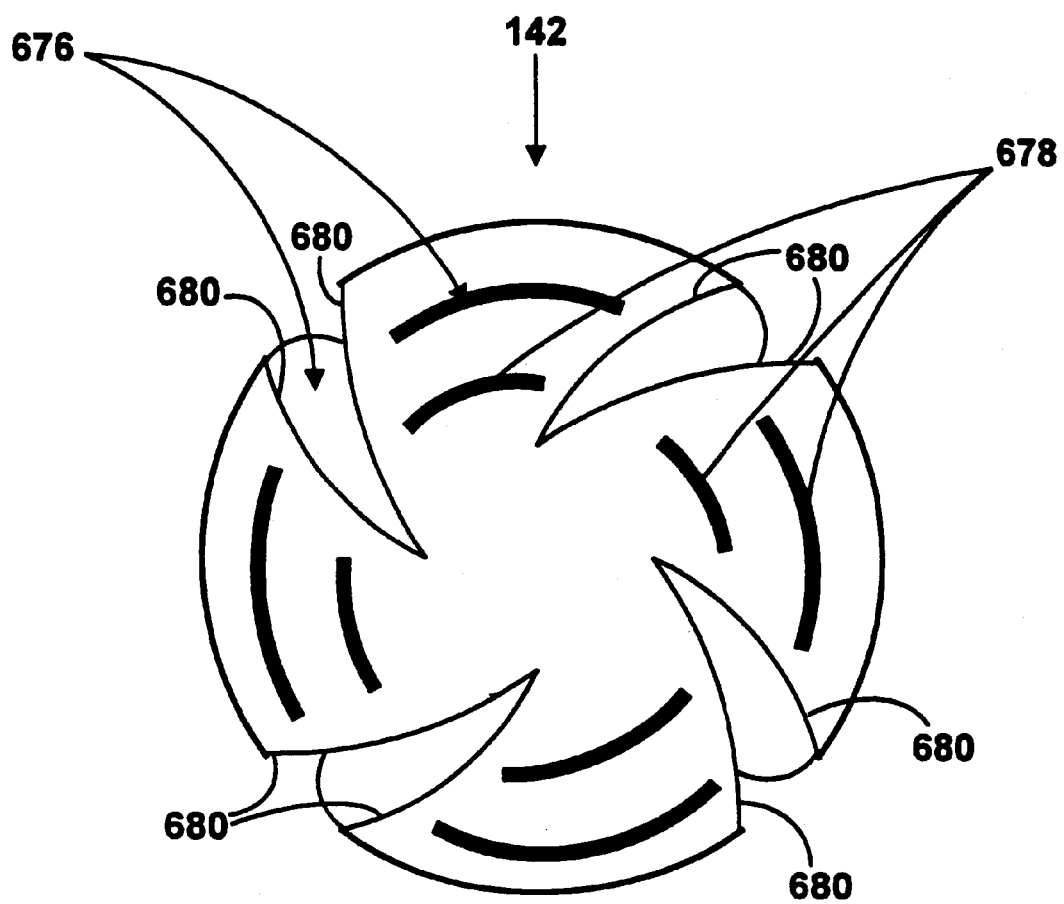

FIG. 6D shows an end-on view of another embodiment of a generally non-conducting tip, featuring various arrangements of the conducting and non-conducting portions. Tip 142 includes conducting portion 678, non-conducting portions 676, and cutting edges 680.

Conducting portion 678 and non-conducting portions 676 are present on the surface of tip 142. Cutting edges 680 are present on the surface of the tip, and in between the conducting and the non-conducting portions.

It can be appreciated that the structures depicted in FIGS. 6A–6D include convex and concave tip surfaces. The coating edges can be defined by the meeting of these convex and concave tip surfaces.

In operation, tip 142 may be moved in a surgical motion, utilizing cutting edges 680. Additionally, electrical power may be supplied to conducting portions 678, which then permit a cauterizing effect to take place. Substantially less or no cauterizing effect takes place at or near non-conductive portions 676.

It will be apparent to those skilled in the art that various modifications and variations can be made in the apparatus and methods of the present invention without departing from the spirit or scope of the invention. Thus, it is intended that the present invention cover the modifications and variations of this invention provided they come within the scope of the appended claims and their equivalents.

What is claimed is:

1. A surgical apparatus, comprising:
    a surgical instrument including a housing and a cannula, the cannula attached at a proximal end to the housing and defining at a distal end thereof an opening, the housing containing a drive interface, the surgical instrument further including a first electrical member suitable for switchable coupling to a power supply, the first electrical member including a brush; and
    a surgical tool including a shaft and a tip, the tip located in the opening and including at least one conducting portion, the shaft contained within the cannula and the shaft mechanically and electrically coupled at a distal end to the tip, and at a proximal end, to the drive interface and an electrical interface, and the drive interface producing a surgical motion of the tip, and the electrical interface producing a cauterizing action at the at least one conducting portion of the tip, the surgical tool further including a second electrical member, located at the proximal end of the shaft and a commutator electrically coupling the first electrical member to the shaft to form the electrical interface.

2. The surgical apparatus of claim 1, wherein the first electrical member includes a switch, located on the housing.

3. The surgical apparatus of claim 1, wherein the surgical instrument further comprises:
    an interconnector including the first electrical member and the interconnector located between the housing and the cannula for coupling the housing and the cannula.

4. The surgical apparatus of claim 1, wherein the second electrical member includes the proximal end of the shaft.

5. The surgical apparatus of claim 1, wherein the tip includes at least one non-conducting portion, and wherein the shaft is electrically coupled to the at least one conducting portion.

6. The surgical apparatus of claim 5, wherein the at least one conducting portion defines at least one exposed convex tip surface and the non-conducting portion defines at least one concave tip surface.

7. The surgical apparatus of claim 5, wherein the at least one conducting portion defines at least one exposed concave tip surface and the non-conducting portion defines at least one convex tip surface.

8. The surgical apparatus of claim 5, wherein the at least one non-conducting portion defines a first exposed surface of the tip, and the at least one conducting portion extends from at least one location internal to the tip through the at least one non-conducting portion to define a second exposed surface of the tip.

9. The surgical apparatus of claim 8, wherein the at least one conducting portion extends from a single location internal to the tip.

10. The surgical apparatus of claim 8, wherein the at least one conducting portion extends from multiple locations internal to the tip.

11. The surgical apparatus of claim 8, wherein the at least one conducting portion extends at an angle to a longitudinal axis of the tip to define at least one disk.

12. The surgical apparatus of claim 8, wherein the second exposed surface extends in a diametric arc about a longitudinal axis of the tip.

13. The surgical apparatus of claim 8, wherein the second exposed surface extends in an arc along a longitudinal axis of the tip.

14. The surgical apparatus of claim 8, wherein the second exposed surface defines at least one point source.

15. The surgical apparatus of claim 8, wherein the second exposed surface defines at least one cutting edge of the tip.

16. The surgical apparatus of claim 1, wherein a substantial portion of a surface of the shaft is conductive, thus forming an electrical coupling between the electrical interface and the tip.

17. The surgical apparatus device of claim 1, wherein a substantial portion of a surface of the shaft is conductive, thus forming an electrical coupling between the electrical interface and the tip.

18. A method of performing a surgical procedure, comprising using the surgical apparatus of claim 1 in the course of performing the surgical procedure.

19. A cutting and cauterizing device for connection to a surgical instrument, the surgical instrument including a drive interface and a first interconnector, the cutting and cauterizing device comprising:
   a cannula defining at a distal end thereof an opening;
   a second interconnector, suitable for switchably coupling to a power supply, the second interconnector located at a proximal end of the cannula and shaped to couple to the first interconnector, the second interconnector further including a first electrical member suitable for switchably coupling to the power supply, the first electrical member including a brush; and
   a surgical tool including a shaft and a tip, the tip located in the opening and including at least one conducting portion, the shaft contained within the cannula, the shaft being coupled at a distal end to the tip and at a proximal end mechanically coupled to the drive interface to permit a surgical motion of the tip, and the shaft electrically coupled to the second interconnector to permit a cauterizing action at the at least one conducting portion of the tip, the surgical tool further comprising a second electrical member located at the proximal end of the shaft and further including a commutator electrically coupling the first electrical member to the shaft.

20. The cutting and cauterizing device of claim 19, wherein the second electrical member includes the proximal end of the shaft.

21. The cutting and cauterizing device of claim 19, wherein the tip includes at least one non-conducting portion, and wherein the shaft is electrically coupled to the at least one conducting portion.

22. The cutting and cauterizing device of claim 21, wherein the at least one conducting portion defines at least one exposed convex tip surface and the non-conducting portion defines at least one concave tip surface.

23. The cutting and cauterizing device of claim 21, wherein the at least one conducting portion defines at least one exposed concave tip surface and the non-conducting portion defines at least one convex tip surface.

24. The cutting and cauterizing device of claim 21, wherein the at least one non-conducting portion defines a first exposed surface of the tip, and the at least one conducting portion extends from at least one location internal to the tip through the at least one non-conducting portion to define a second exposed surface of the tip.

25. The cutting and cauterizing device of claim 24, wherein the at least one conducting portion extends from a single location internal to the tip.

26. The cutting and cauterizing device of claim 24, wherein the at least one conducting portion extends from multiple locations internal to the tip.

27. The cutting and cauterizing device of claim 24, wherein the at least one conducting portion extends at an angle to a longitudinal axis of the tip to define at least one disk.

28. The cutting and cauterizing device of claim 24, wherein the second exposed surface extends in a diametrical arc about a longitudinal axis of the tip.

29. The cutting and cauterizing device of claim 24, wherein the second exposed surface extends in an arc along a longitudinal axis of the tip.

30. The cutting and cauterizing device of claim 24, wherein the second exposed surface defines at least one point source.

31. The cutting and cauterizing device of claim 24, wherein the second exposed surface defines at least one cutting edge of the tip.

32. A method of performing a surgical procedure, comprising using the cutting and cauterizing device of claim 19 in the course of performing the surgical procedure.

33. A surgical apparatus, comprising:
   a surgical instrument including a housing and a cannula, the cannula attached at a proximal end to the housing and defining at distal end thereof an opening and the housing containing a drive interface; and
   a surgical tool including a shaft and a tip, the tip located in the opening and including at least one conducting portion, the shaft contained within the cannula and the shaft mechanically and electrically coupled at a distal end to the tip, and at a proximal end, to the drive interface and an electrical interface, and the drive interface producing a surgical motion of the tip, and the electrical interface producing a cauterizing action at the at least one conducting portion of the tip,
   wherein the drive interface is located adjacent to a drive coupling and a commutator, the commutator being located at the proximal end of the shaft, and
   the surgical motion of the tip includes rotary motion of the at least one conducting portion of the tip.

* * * * *